US010695296B2

(12) United States Patent
Shah et al.

(10) Patent No.: US 10,695,296 B2
(45) Date of Patent: *Jun. 30, 2020

(54) FORMULATIONS, METHODS, KIT, AND DOSAGE FORMS FOR IMPROVED STABILITY OF AN ACTIVE PHARMACEUTICAL INGREDIENT

(71) Applicant: Asana BioSciences, LLC, Lawrenceville, NJ (US)

(72) Inventors: Navnit Shah, Bridgewater, NJ (US); Harpreet Sandhu, Bridgewater, NJ (US); Ashish Chatterji, Bridgewater, NJ (US); Helen Usansky, Hillsborough, NJ (US); Louis Denis, Princeton, NJ (US); Niranjan Rao, Monroeville, NJ (US); Sarper Toker, Collegeville, PA (US)

(73) Assignee: Asana BioSciences, LLC, Lawrenceville, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 16/035,771

(22) Filed: Jul. 16, 2018

(65) Prior Publication Data

US 2019/0015337 A1    Jan. 17, 2019

Related U.S. Application Data

(60) Provisional application No. 62/532,572, filed on Jul. 14, 2017, provisional application No. 62/556,010, filed on Sep. 8, 2017, provisional application No. 62/577,445, filed on Oct. 26, 2017.

(51) Int. Cl.
| | |
|---|---|
| *A61K 9/16* | (2006.01) |
| *A61K 9/50* | (2006.01) |
| *A61K 9/28* | (2006.01) |
| *A61K 9/20* | (2006.01) |
| *A61K 9/48* | (2006.01) |
| *A61K 9/00* | (2006.01) |
| *C07D 471/04* | (2006.01) |

(52) U.S. Cl.
CPC .......... *A61K 9/1652* (2013.01); *A61K 9/0053* (2013.01); *A61K 9/0056* (2013.01); *A61K 9/1611* (2013.01); *A61K 9/1617* (2013.01); *A61K 9/1623* (2013.01); *A61K 9/1694* (2013.01); *A61K 9/2013* (2013.01); *A61K 9/2018* (2013.01); *A61K 9/2054* (2013.01); *A61K 9/28* (2013.01); *A61K 9/485* (2013.01); *A61K 9/4858* (2013.01); *A61K 9/4866* (2013.01); *A61K 9/50* (2013.01); *A61K 9/5015* (2013.01); *A61K 9/5026* (2013.01); *A61K 9/5042* (2013.01); *C07D 471/04* (2013.01); *C07B 2200/13* (2013.01)

(58) Field of Classification Search
CPC ... A61K 9/16; A61K 9/50; A61K 9/28; A61K 9/20; A61K 9/48; A61K 9/00; A61K 9/2054; A61K 9/2018; A61K 9/2013; A61K 9/4866; A61K 9/4858; A61K 9/485; A61K 9/0056; A61K 9/0053; C07D 47/04

See application file for complete search history.

(56) References Cited

U.S. PATENT DOCUMENTS 9,499,495 B2 * 11/2016 Thompson ........... C07D 413/14
9,572,808 B2 *  2/2017 Zhu ..................... A61K 31/498
(Continued)

FOREIGN PATENT DOCUMENTS

WO    2012/118492 A1    9/2012

OTHER PUBLICATIONS

Jhon Jairo Rojas Camargo Theses and Dissertations (2011).*
(Continued)

*Primary Examiner* — Shirley V Gembeh
(74) *Attorney, Agent, or Firm* — DLA Piper LLP (US)

(57) ABSTRACT

Embodiments of the disclosure relate generally to formulations, methods, kits, and dosage forms for improved stability of an active pharmaceutical ingredient, wherein the active ingredient comprises a compound of the formula:

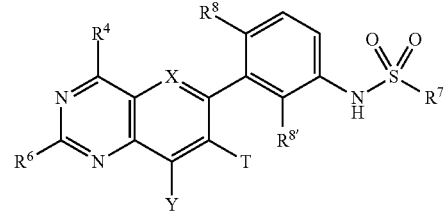

wherein X is N, Y is H or optionally substituted $C_1$-$C_6$ alkyl; $R^4$ is morpholine optionally substituted with by $C_1$-$C_6$ alkyl; $R^7$ is $C_1$-$C_6$ alkyl optionally substituted by one or more F; $R^{8'}$ is halogen; and $R^6$ is

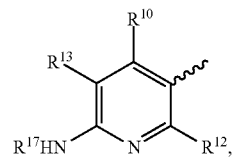

wherein $R^{10}$ is H, $C_1$-$C_6$ alkyl, halogen, CN or $CF_3$; $R^{12}$ is H or halogen; $R^{13}$ is H, halogen or $C_1$-$C_6$ alkyl; and $R^{17}$ is H, $C_1$-$C_6$ alkyl, ($C_1$-$C_6$ alkyl)-$NH_2$; and, pharmaceutically acceptable salts and free bases thereof, wherein the active ingredient remains in substantially amorphous form after storage of the pharmaceutical formulation for a predetermined time and conditions. In one embodiment the formulations, methods, kits and dosage forms comprising the active pharmaceutical ingredient with improved stability can be used in the treatment of a condition characterized by the dysregulation of one of both of the RAS/RAF/MEK/ERK and PI3K/AKT/PTEN/mTOR pathways.

28 Claims, 26 Drawing Sheets

(56) References Cited

U.S. PATENT DOCUMENTS

2008/0182870 A1    7/2008   Bondy et al.
2010/0204222 A1    8/2010   Newlander et al.
2017/0027953 A1    2/2017   Thompson et al.

OTHER PUBLICATIONS

International Search Report and Written Opinion from counterpart Application No. PCT/US2018/042264 dated Sep. 21, 2018.
International Preliminary Report on Patentability from counterpart Application No. PCT/US2018/042264 dated Jan. 23, 2020.

\* cited by examiner

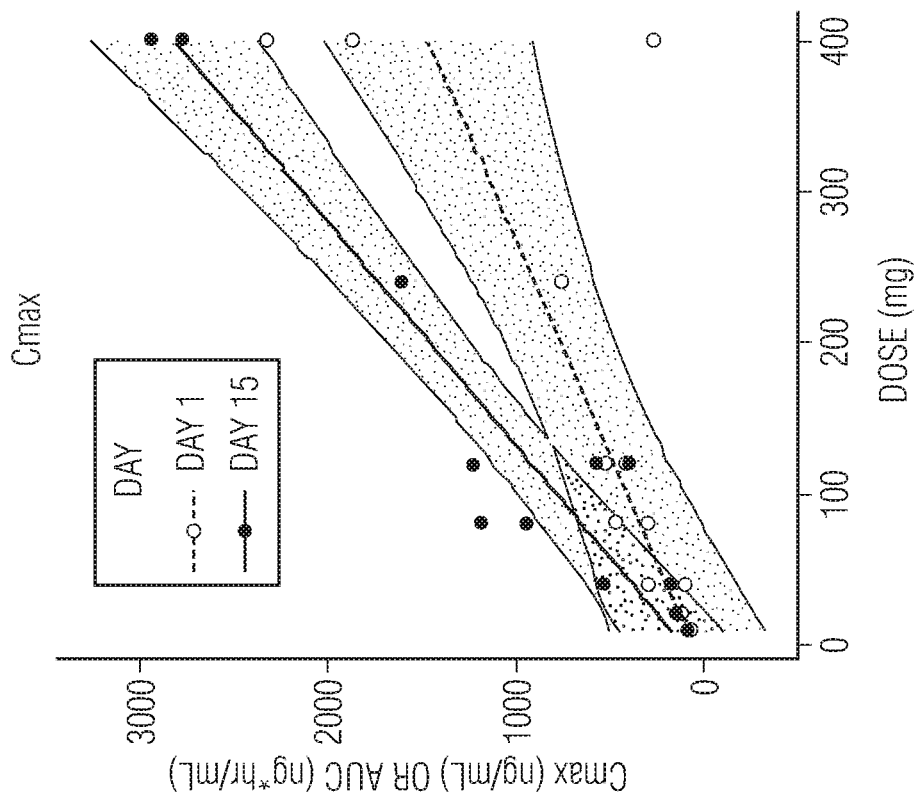
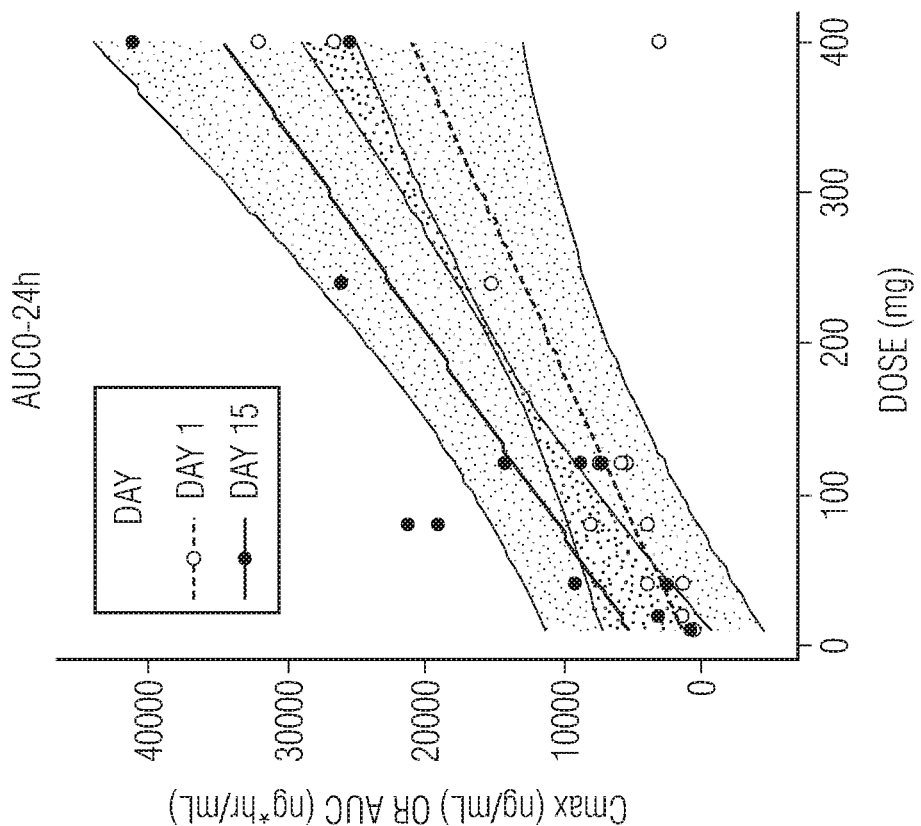

FORMULATIONS, METHODS, KIT, AND DOSAGE FORMS FOR IMPROVED STABILITY OF AN ACTIVE PHARMACEUTICAL INGREDIENT

TECHNICAL FIELD

Embodiments of the disclosure relate generally to formulations, methods, kits, and dosage forms for improved stability of an active pharmaceutical ingredient. In one embodiment the formulations, methods, kits and dosage forms comprising the active pharmaceutical ingredient with improved stability can be used in the treatment of cancers.

BACKGROUND

The RAS/RAF/MEK/ERK (or "RAS") and PI3K/AKT/PTEN/mTOR (or "PI3K") signaling pathways play an important role in the initiation and progression of tumors. The RAS pathway is known to be dysregulated through genetic mutations in RAS, RAF or MEK genes, which leads to increased cell proliferation and angiogenesis. These genetic mutations have been found in wide variety tumors, and inhibition of any of these targets was found to inhibit the growth of tumors both in preclinical animal models and in humans. Similar to the RAS pathway, perturbations in the PI3K pathway also plays an important role in tumor progression, specifically in promoting the tumor cell survival and proliferation. This pathway is dysregulated through genetic changes in the PI3K, AKT and PTEN genes.

Despite some promising initial results in humans, compounds designed to inhibit either the RAS or PI3K pathway are not able to provide a durable therapeutic response, due to drug resistance acquired by the tumor cells from activation of the alternative pathway in the targeted cells. For example, the inhibition of the PI3K pathway with agents such as temsirolimus leads to the subsequent activation of the RAS pathway, resulting in tumors which do not respond to this agent. Conversely, inhibition of the RAS pathway with agents such as vemurafenib leads to the activation of PI3K pathway and the development of drug-resistant tumor cells.

Preclinical data obtained using different combinations of two agents, each inhibiting either the RAS or PI3K pathways, has demonstrated that the simultaneous inhibition of these pathways gives a greater and more durable tumor growth inhibition. However, combining two different agents in this manner can produce the significant disadvantages of added toxicity and higher cost for any subsequently developed drug. Single compounds with dual inhibitory activity against both pathways have since been discovered; see, for example, U.S. Pat. No. 9,499,495 of Thompson et al, "Quinazolines and Azaquinazolines as Dual Inhibitors of RAS/RAF/MEK/ERK and PI3K/AKT/PTEN/MTOR Pathways." Such compounds avoid the disadvantages of drugs which combine two separate inhibitory compounds. Thus there is a need for stable formulations of single compounds which regulate both the RAS and PI3K pathways, which can be incorporated into dosage forms and kits, all of which can be used in methods treating cancers characterized by the presence of solid tumors.

SUMMARY

The present disclosure relates to formulations, methods, kits, and dosage forms for treating conditions related to the dysregulation of one or both of the RAS/RAF/MEK/ERK and PI3K/AKT/PTEN/MTOR pathways, such as inflammatory disorders or cancers characterized by the presence of solid tumors, particularly melanoma, colon cancer, non-small cell lung cancer, bladder cancer and breast cancer. In an embodiment, the present disclosure provides a pharmaceutical formulation comprising an active ingredient in substantially amorphous form and one or more stabilizing polymers, wherein the active ingredient comprises a compound of the formula (I):

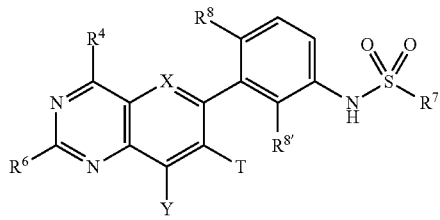

Wherein X is N, Y is H or optionally substituted $C_1$-$C_6$ alkyl; $R^4$ is morpholine optionally substituted with by $C_1$-$C_6$ alkyl; $R^7$ is $C_1$-$C_6$ alkyl optionally substituted by one or more F; $R^{8'}$ is halogen; and $R^6$ is

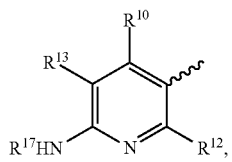

wherein $R^{10}$ is H, $C_1$-$C_6$ alkyl, halogen, CN or $CF_3$; $R^{12}$ is H or halogen; $R^{13}$ is H, halogen or $C_1$-$C_6$ alkyl; and $R^{17}$ is H, $C_1$-$C_6$ alkyl, ($C_1$-$C_6$ alkyl)-$NH_2$; and enantiomers, pharmaceutically acceptable salts and free bases thereof, wherein the active ingredient remains in substantially amorphous form after storage of the pharmaceutical formulation for a predetermined time and under predetermined conditions.

In another embodiment, the present disclosure provides a dosage form comprising a pharmaceutical formulation comprising an active ingredient of formula (I) in substantially amorphous form and one or more stabilizing polymers, wherein the active ingredient remains in substantially amorphous form after storage of the pharmaceutical formulation for a predetermined time and under predetermined conditions.

In another embodiment, the present disclosure provides a method of manufacturing or stabilizing a pharmaceutical formulation, comprising the steps of dissolving an active ingredient comprising a compound of formula (I) and one or more polymer stabilizers in an excess of organic solvent to form a mixture, and spray-granulating or bead-layering the second mixture with a particulate carrier to form the pharmaceutical formulation, wherein the active ingredient remains in substantially amorphous form after storage of the pharmaceutical formulation for a predetermined time and under predetermined conditions. In a further embodiment, one or more anti-static agents are added to the mixture to prior to spray granulating or bead layering.

In another embodiment, the present disclosure provides a method of manufacturing or stabilizing a pharmaceutical formulation, comprising the steps of dissolving an active ingredient comprising a compound of formula (I) and one or more polymer stabilizers in an excess of organic solvent to form a first mixture, and spray-drying the second mixture to form the pharmaceutical formulation, wherein the active ingredient remains in substantially amorphous form after storage of the pharmaceutical formulation for a predetermined time and conditions. In a further embodiment, one or more anti-static agents are added to the mixture to prior to spray drying.

In another embodiment, the present disclosure provides a kit comprising one or more dosage forms and instructions for administering the dosage forms to a subject, wherein the dosage forms comprise a pharmaceutical formulation comprising an active ingredient in substantially amorphous form and one or more stabilizing polymers, wherein the active ingredient comprises a compound of the formula (I), wherein the active ingredient remains in substantially amorphous form after storage of the pharmaceutical formulation for a predetermined time and under predetermined conditions.

In another embodiment, the present disclosure provides a method of treating a condition characterized by the dysregulation of one or both of the RAS/RAF/MEK/ERK and PI3K/AKT/PTEN/mTOR pathways in a subject, comprising administering to the subject a therapeutically effective amount of an active ingredient in one or more dosage forms, wherein the dosage forms comprise a pharmaceutical formulation comprising an active ingredient in substantially amorphous form and one or more stabilizing polymers, wherein the active ingredient comprises a compound of the formula (I), wherein the active ingredient remains in substantially amorphous form after storage of the pharmaceutical formulation for a predetermined time and under predetermined conditions.

In another embodiment, the present disclosure provides a method of preparing a crystalline form of N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide, comprising the steps of dissolving the solid compound in acetone under heat, allowing the resulting solution to cool to 40-50° C., filtering the cooled solution to remove any insoluble particulate matter to produce a filtrate, and evaporating the filtrate under reduced pressure to obtain a crystalline solid. In a further embodiment, the obtained crystalline solid is then dried under vacuum at 60-65° C.

BRIEF DESCRIPTION OF THE DRAWINGS

FIGS. 12A to 12C are graphs showing the kinetics in dog plasma of: FIG. 12A, an orally-dosed control formulation of the sodium salt of the active ingredient, 1% copovidone, and 5% w/v TPGS in purified water, as a solution ("Formulation 1"); FIG. 12B, an orally-dosed hot-melt extruded formulation of 24% w/w of the active ingredient, 72.5% w/w copovidone and 3.5% colloidal silicon dioxide powder ("Formulation 2") in a vehicle containing 2% w/v hydroxypropylcellulose and 0.1% Polysorbate 80 in purified water; and FIG. 12C, an orally-dosed formulation of spray-dried amorphous active ingredient and HPMC-AS (25:75) ("Formulation 3") in a vehicle containing 2% w/v hydroxypropylcellulose and 0.1% Polysorbate 80 in purified water. In each graph, the X axis is time in hours, and the Y axis is the concentration of the active ingredient in nanograms per milliliter.

FIG. 14A: Patient 101-002 at 10 mg QD. FIG. 14N: Patient 104-001 at 400 mg QD.

FIG. 16A is a graph showing the dose-dependent steady state AUC and FIG. 16B is a graph showing the dose-dependent steady state Cmax in subjects treated with a pharmaceutical formulation of the present disclosure, in particular CMPD A.

DETAILED DESCRIPTION

Figure 1:
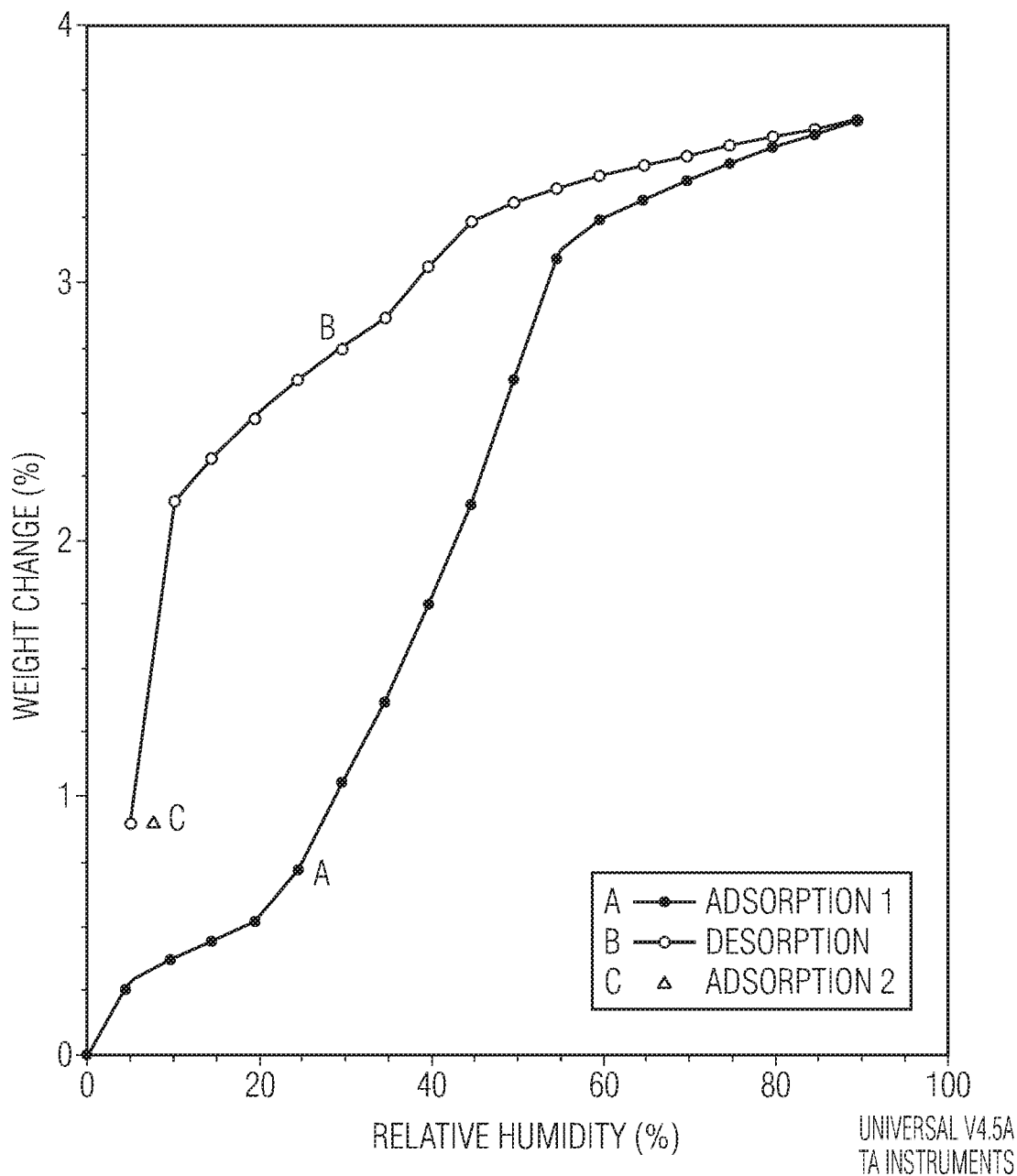
FIG. 1 is a graph showing the percent weight change for unstabilized active ingredient N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide exposed to increasing relative humidity.

The following detailed description is exemplary and explanatory and is intended to provide further explanation of the present disclosure described herein. Other advantages, and novel features will be readily apparent to one of ordinary skill in the art from the following detailed description of the present disclosure.

The disclosure provides one or more powder pharmaceutical formulations, methods of manufacturing, kits, methods of treating, and dosage forms further comprising an active ingredient configured to regulate both the RAS/RAF/MEK/ERK ("RAS") and PI3K/AKT/PTEN/mTOR ("PI3K"), such that they are capable of treating conditions associated with dysregulation in one or both of these pathways, including, for example, cancers and inflammatory disorders.

In one embodiment, a pharmaceutical formulation of the disclosure comprises an active ingredient in substantially amorphous form and one or more stabilizing polymers, wherein the active ingredient comprises a compound of the formula (I):

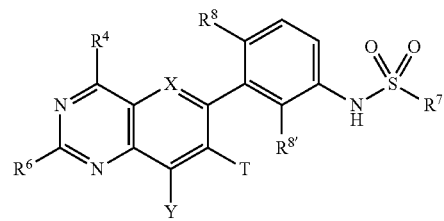

wherein X is N, Y is H or optionally substituted $C_1$-$C_6$ alkyl; $R^4$ is morpholine optionally substituted with by $C_1$-$C_6$ alkyl; $R^7$ is $C_1$-$C_6$ alkyl optionally substituted by one or more F; $R^{8'}$ is halogen; and $R^6$ is

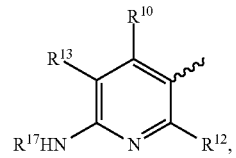

wherein $R^{10}$ is H, $C_1$-$C_6$ alkyl, halogen, CN or $CF_3$; $R^{12}$ is H or halogen; $R^{13}$ is H, halogen or $C_1$-$C_6$ alkyl; and $R^{17}$ is H, $C_1$-$C_6$ alkyl, ($C_1$-$C_6$ alkyl)-$NH_2$; and enantiomers, pharmaceutically acceptable salts and free bases thereof, wherein the active ingredient remains in substantially amorphous form after storage of the pharmaceutical formulation for a predetermined time and conditions. In one embodiment, the pharmaceutically acceptable salt is one of hydrochloride, 4-methyl-benzene sulfonic acid, benzene sulfonic acid, methane-sulfonic acid, sulfuric acid, or nitric acid salt, or the like. In another embodiment, an active ingredient of the disclosure comprises the free base of compounds of formula (I).

Compounds of formula (I) possess one or more chiral centers, and it is specifically contemplated that each separate enantiomer of compounds comprising an active ingredient of the disclosure, as well as mixtures of the enantiomers, can be used in the present formulations and methods. As disclosed herein, all chiral, enantiomeric and racemic forms of a chemical structure are intended, unless the specific stereochemistry is indicated. It is well known in the art how to prepare optically active forms of the compounds comprising active ingredients of the present formulations and methods, such as by resolution of racemic forms or by synthesis from optically active starting materials.

In one embodiment, the active ingredient comprises one or more of the following compounds:

N-(3-(2-(2-aminopyrimidin-5-yl)-4-morpholinopyrido[3,2-d]pyrimidin-6-yl)-2-fluorophenyl)-3-fluoropropane-1-sulfonamide;

N-(3-(2-(6-aminopyridin-3-yl)-4-morpholinopyrido[3,2-d]pyrimidin-6-yl)-2-fluorophenyl)-3-fluoropropane-1-sulfonamide;

3-fluoro-N-(2-fluoro-3-(4-morpholino-2-(1H-pyrrolo[2,3-b]pyridin-5-yl)pyrido[3,2-d]pyrimidin-6-yl)phenyl)propane-1-sulfonamide;

N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide;

3-fluoro-N-(2-fluoro-3-(2-(6-(methylamino)pyridin-3-yl)-4-morpholinopyrido[3,2-d]pyrimidin-6-yl)phenyl)propane-1-sulfonamide;

(S)—N-(3-(2-(6-amino-4-fluoropyridin-3-yl)-4-(3-methylmorpholino)pyrido[3,2-d]pyrimidin-6-yl)-2-fluorophenyl)-3-fluoropropane-1-sulfonamide; or (S)—N-(3-(2-(6-amino-4-(trifluoromethyl)pyridin-3-yl)-4-(3-methylmorpholino)pyrido[3,2-d]pyrimidin-6-yl)-2-fluorophenyl)-3-fluoropropane-1-sulfonamide.

In another embodiment, the active ingredient comprises N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide (also referred to herein and in the Figures as CMPD A).

Active ingredients of the present disclosure can be prepared, for example, according to the methods disclosed in U.S. Pat. No. 9,499,495, the entire disclosure of which is herein incorporated by reference. In some embodiments of the disclosure, an active ingredient comprising the pharmaceutical formulation of the disclosure can be present in at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5%, 99.9% or 100% w/w.

The active ingredient for use in the present formulations and methods is a single compound which regulates both the RAS and PI3K pathways. The dual regulatory activity of the active ingredients of the disclosure makes these compounds useful for manufacturing pharmaceutical formulations, which can be used for treating conditions such as inflammatory disorders or cancers characterized by the presence of solid tumors, particularly melanoma, colon cancer, non-small cell lung cancer, bladder cancer and breast cancer. Where the active ingredient is N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide, the active ingredient has a molecular mass of 609.16, a critical temperature of 1107 Kelvin, Gibbs energy of 106.25 kJ/mol, a Log P of 4.22 and a c Log P of 3.2.

The active ingredients of the present disclosure are hygroscopic, and tend to form multiple crystal forms upon hydration at room temperature. Such crystal forms themselves may unstable, and the active ingredients can migrate through several different crystal forms depending on the level of hydration and the length of storage time. Such instability is unacceptable in a pharmaceutical formulation, where the active ingredient must be maintained in a stable form up through administration to a subject. It has now been surprisingly found that the active ingredients of the disclosure can be stabilized in substantially amorphous form by combining them with certain stabilizing polymers, and the active ingredient in the resulting pharmaceutical formulation can be maintained in a substantially amorphous state throughout manufacture and storage without the formation of unstable crystal forms.

The present disclosure thus provides for stable or stabilized pharmaceutical formulations comprising an active ingredient of the disclosure as described herein, for example stable or stabilized formulations comprising one or more compounds of formula (I), or enantiomers, pharmaceutically acceptable salts or free bases thereof. The stability of a formulation according to the present disclosure can be determined, for example, by measuring the physical state of the active ingredient. In one embodiment, the active ingredient remains in substantially amorphous form after storage for predetermined times and under predetermined conditions.

As used herein, the term "substantially amorphous" means that most of the active ingredient in a given pharmaceutical composition is amorphous. In certain embodiments, substantially amorphous means that about 95%, 96%, 97%, 98%, 99%, 99.1%, 99.2%, 99.3%, 99.4%, 99.5%, 99.6%, 99.7%, 99.8%, 99.9% or 100% of the active ingredient is in amorphous form.

Any suitable technique can be used to determine whether an active ingredient of the present pharmaceutical formulations remains in amorphous form or has converted to a crystalline form. For example, the physical state of the active ingredient can be determined by X-ray powder diffraction ("XRPD") under conditions as described, e.g., in Example 1 below.

As discussed above, the active ingredient of the present disclosure is maintained in substantially amorphous form by combining the active ingredients with one or more polymeric stabilizers. Suitable polymeric stabilizers for use according to the present disclosure include polyvinylpyrrolidone and hydroxypropylmethyl cellulose acetate succinates.

Polyvinylpyrrolidone (PVP or copovidone) is a vinylpyrrolidone-vinyl acetate copolymer soluble in water and most polar solvents. Any type or grade of polyvinylpyrrolidone can be used in the formulations of the disclosure. In one embodiment, the polyvinylpyrrolidone used in the formulations of the disclosure is a copolymer of 1-vinyl-2-pyrrolidone and vinyl acetate in a ratio of 6:4 by mass, with a weight-average molecular weight, for example, in the range of 45,000-70,000, such as Kollidone® VA64 which can be obtained from (BASF AG, Ludwigshafen, Germany).

Hydroxypropylmethyl cellulose acetate succinates, also called hypromellose acetate succinates or "HPMC-AS" are a mixture of acetic acid and monosuccinic acid esters of hydroxypropyl methylcellulose. In certain forms, they can contain not less than about 12 percent and not more than about 28 percent of methoxy groups (—OCH3), not less than about 4 percent and not more than about 23 percent of hydroxypropoxy groups (—OCH2CHOHCH3), not less than about 2 percent and not more than about 16 percent of acetyl groups (—COCH3), or not less than about 4 percent and not more than about 28 percent of succinoyl groups (—COC2H4COOH), calculated on the dried basis. HPMC-AS polymers can be divided into different grades, based for example on viscosity and the percentages of methoxy, hydroxypropoxy, acetyl and succinyl groups, for example as shown in the following Table 1.

TABLE 1

Hydroxypropylmethyl Cellulose Acetate Succinate Grades

| | | AS-L | | | AS-M | | | AS-H | | |
|---|---|---|---|---|---|---|---|---|---|---|
| | | \multicolumn{9}{c}{Sample ID} |
| | | A | B | C | D | E | F | G | H | I |
| Viscosity | mPa-s | 3.15 | 3.00 | 3.10 | 3.14 | 2.74 | 3.01 | 3.12 | 2.83 | 2.92 |
| Methoxy | % | 22.3 | 22.5 | 22.6 | 22.7 | 23.1 | 23.1 | 23.5 | 23.6 | 23.8 |

TABLE 1-continued

Hydroxypropylmethyl Cellulose Acetate Succinate Grades

| | | Grade | | | | | | | | |
|---|---|---|---|---|---|---|---|---|---|---|
| | | AS-L | | | AS-M | | | AS-H | | |
| | | Sample ID | | | | | | | | |
| | | A | B | C | D | E | F | G | H | I |
| Hydroxypropoxy | % | 6.7 | 7.2 | 7.0 | 6.9 | 7.2 | 7.1 | 7.2 | 7.4 | 7.2 |
| Succinoyl | % | 18.1 | 15.0 | 14.0 | 14.2 | 11.4 | 9.9 | 8.0 | 7.7 | 4.1 |
| Acetyl | % | 5.7 | 7.9 | 8.4 | 7.5 | 9.1 | 10.6 | 10.7 | 11.6 | 13.9 |

Any grade of HPAS can be used to make the formulations and dosage forms of the present disclosure. In certain embodiments, the pharmaceutical formulations of the disclosure comprise HPMC-AS grade AS-L. Suitable HPMC-AS polymers can be obtained from Shin-Etsu Chemical Co., Ltd., Tokyo, Japan or from SE Tylose USA, Inc., Totowa, N.J.

The method by which the active ingredient and stabilizing polymer is formulated can also affect stability. For example, formulating an active ingredient of the disclosure with a polyvinylpyrrolidone as a hot melt extrusion can result in the active ingredient crystallizing at higher temperatures. Hot melt extrusion with HPMC-AS or Eudragit polymers can result in a high level of active ingredient degradation. Nevertheless, hot melt extrusion, for example as demonstrated in the Examples below, can be used to produce formulations comprising active ingredients of the disclosure in which the active ingredient remains in amorphous form throughout the manufacturing process, during storage under various conditions of temperature and humidity or when suspended in various solutions. Any suitable hot melt extrusion technique can be used to produce formulations of the disclosure, for example as described in the Examples below. In certain embodiments, the hot melt extruded formulation is milled to produce particles, which can be used to make dosage forms such as tablets or capsules, either alone or when combined with suitable pharmaceutical excipients.

Pharmaceutical formulations comprising active ingredients and stabilizing polymers of the disclosure can also be spray dried, spray granulated or produced by bead-layering. The active ingredient in such spray-dried, spray granulated or bead-layered formulations remains in the amorphous form throughout the manufacturing process, during storage under various conditions of temperature and humidity or when suspended in various solutions. Any suitable spray drying, spray granulating or bead-layering technique can be used to produce formulations of the disclosure. Exemplary spray drying and spray granulating methods for producing pharmaceutical formulations of the disclosure are described in the Examples below.

In some embodiments, the formulations of the disclosure are stable when subject to predetermined conditions for predetermined times. For example, pharmaceutical formulations of the disclosure can be stored at various predetermined temperatures and relative humidities for defined or predetermined time periods, for example in an open or closed container. In some embodiments, formulations of the disclosure are stable upon storage at about 5, 25, 30, 37, 40 or 45 degrees Celsius and about 0%, 5%, 10%, 15%, 20%, 25%, 30%, 35%, 40%, 45%, 50%, 55%, 60%, 65%, 70%, 75%, 80%, 85%, 90%, 95% or 100% relative humidity for a period of at least about 0.5, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 20, 25, 30, 35, 40, 45, 48, 50, 51, 52, 53, 55 or 60 hours 1 week, 2 weeks, 3 weeks or 4 week; 1 month, 2 months, 3 months, 4 months, 5 months or 6 months.

In certain embodiments, formulations of the disclosure are stable upon storage in an open or closed container at: about 30 degrees Celsius and about 90 percent relative humidity for a period of at least about 20 hours; about 40 degrees Celsius and about 60 percent relative humidity for a period of at least about one week, two weeks or three weeks; about 40 degrees Celsius and about 75 percent relative humidity for a period of at least about one week, two weeks or three weeks; about 25 degrees Celsius and about 60 percent relative humidity for a period of at least about one month; about 40 degrees Celsius and about 75 percent relative humidity for a period of at least one month; about 25 degrees Celsius and about 75 percent relative humidity for a period of at least about 3 months; or 5 degrees Celsius at any relative humidity for a period of at least about three months. In some embodiments, "storage in an open container" means that the container was opened twice a day for a given period of time, for example up to four weeks, but was otherwise left closed.

In another embodiment, the formulation comprises N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide and is stable upon storage in an open or closed container at: about 30 degrees Celsius and about 90 percent relative humidity for a period of at least about 20 hours; about 40 degrees Celsius and about 60 percent relative humidity for a period of at least about one week, two weeks or three weeks; about 40 degrees Celsius and about 75 percent relative humidity for a period of at least about one week, two weeks or three weeks; about 25 degrees Celsius and about 60 percent relative humidity for a period of at least about one month; about 40 degrees Celsius and about 75 percent relative humidity for a period of at least one month; about 25 degrees Celsius and about 75 percent relative humidity for a period of at least about 3 months; or 5 degrees Celsius at any relative humidity for a period of at least about three months.

Stability of the pharmaceutical formulations of the disclosure can also be measured by testing other physical characteristics, for example by testing the dissolution of the formulation at the end of a predetermined time period after it has been subjected to predetermined conditions of, for example, temperature and relative humidity for predetermined periods of time. Suitable methods for measuring the dissolution profile of the present formulations are known in the art. Exemplary methods for measuring the dissolution profile of the present formulations are either a basket dissolution test or paddle dissolution test, for example in simulated gastric fluid, as shown in the Examples below. In some embodiments, the dissolution test comprises placing a formulation or dosage form of the disclosure in 900 mL of 0.05N HCl at 37 degrees Celsius at a 100 rpm basket rotation speed or in 500 ml 0.01 N HCl or 50 mM phosphate buffer (pH 6.8), 0.5% sodium lauryl sulfate with a paddle speed of 50 rpm. In certain embodiments, formulations of the disclosure are substantially fully dissolved at about 10 minutes or at about 20 minutes after initiating the dissolution test.

In other embodiments, the dissolution tests comprise placing a formulation or dosage form of the disclosure comprising N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide in 900 mL of 0.05N HCl at 37 degrees Celsius at a 100 rpm basket rotation speed or in 500 ml 0.01 N HCl or 50 mM phosphate buffer (pH 6.8), 0.5% sodium lauryl sulfate with a paddle speed of 50 rpm. In certain embodiments, such formulations are substantially fully dissolved at about 10 minutes or at about 20 minutes after initiating the dissolution test.

In some embodiments, the active ingredient in the pharmaceutical formulations of the disclosure can comprise an amount of about 0.5 to 100 percent by weight, for example about 0.5, 1, 1.5, 2, 2.5, 5, 10, 15, 20, 25, 30, 35, 40, 45, 50, 55, 60, 65, 70, 75, 80, 85, 90, 95, 96, 97, 98, 99 or 100 percent by weight. In another embodiment, the active ingredient comprises about 24 percent or about 25 percent of the pharmaceutical formulation by weight.

In certain embodiments, formulations of the disclosure comprise an active ingredient of the disclosure, such as N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide, formed into dosage forms such as tablets, capsules, sachets, powders, suspensions, suppositories and the like. In such dosage forms of the disclosure, the amount of active ingredient comprising the dosage form can be any suitable amount, for example about 0.5, 1, 1.5, 2, 2.5, 5, 10, 15, 20, 25, 30, 35, 40, 45, 50, 55, 60, 65, 70, 75, 80, 85, 90, 95, 96, 97, 98, 99 or 100 mg per unit dosage form. In certain embodiments, dosage forms of the disclosure comprise about 25, 50, 75, 80 or 100 mg of the active ingredient per dosage form, for example of N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide.

Although exemplary amounts or ranges for the active ingredient and stabilizing polymer are given, pharmaceutical formulations of the disclosure can comprise any amount of these components suitable for the purposes of obtaining the desirable pharmacologic and stability properties as described herein. In addition to the stabilizing polymer and the active ingredient, pharmaceutical compositions of the disclosure can also comprise other pharmaceutically acceptable excipients, for example adjuvants, antioxidants, binders, buffers, coatings, coloring agents, compression aids, diluents, disintegrants, emulsifiers, emollients, encapsulating materials, fillers, flavoring agents, glidants, granulating agents, lubricants, metal chelators, osmo-regulators, pH adjustors, preservatives, solubilizers, sorbents, stabilizers, sweeteners, surfactants, suspending agents, thickening agents, or viscosity regulators. Suitable excipients for use in pharmaceutical compositions of the disclosure are described, for example, in the "Handbook of Pharmaceutical Excipients", 5th Edition, Eds.: Rowe, Sheskey, and Owen, APhA Publications (Washington, D.C.), Dec. 14, 2005, the disclosure of which is incorporated herein by reference.

In certain embodiments, pharmaceutical compositions of the disclosure can be compacted into a unit dose form, e.g., tablet or caplet, or added to unit dose form, e.g., a capsule.

In a further embodiment, pharmaceutical compositions of the disclosure can be formulated for administration as a powder or suspension. A pharmaceutical formulation of the disclosure which comprises a powder can, for example, be sprinkled on or mixed with a semi-solid carrier such as apple sauce or another food item for administration to a subject. The powder can also, for example, be added to a liquid carrier suitable for administration to subjects, such as a solution of about 2% w/V hydroxypropyl cellulose and about 0.1% w/V polysorbate 80 in water or about 0.2% hydroxypropylcellulose, and 0.1% Tween 80 in water, to form a suspension.

In one embodiment, the dosage form of the disclosure comprises a tablet, for example at about 25, 50, 75, 80 or 100 mg strengths. In another embodiment, the dosage form of the disclosure comprises a capsule, for example at about 25, 50, 75, 80 or 100 mg strengths. In a further embodiment, the dosage form of the disclosure is a tablet comprising N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide, for example at about 25, 50, 75, 80 or 100 mg strengths. In another embodiment, the dosage form of the disclosure is a capsule comprising N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide, for example at about 25, 50, 75, 80 or 100 mg strengths.

Suitable techniques for formulating pharmaceutical compositions of the disclosure into tablets are well-known in the art, and can comprise mixing the active ingredient and stabilizing polymer with one or more pharmaceutically acceptable tableting excipients and compressing the mixture into a tablet, for example with a tableting press. The amount and nature of the tableting excipients used can be readily chosen based on the desired characteristics of the tablet, such as size, hardness, friability and the like. Tablets comprising pharmaceutical compositions of the disclosure can also be coated, for example with film coatings like Opadry White®, or with enteric coatings designed to prevent dissolution of the tablets until the transit the stomach and/or upper intestine. Suitable tablet coatings and methods for applying them are well-known in the art.

Suitable techniques for formulating pharmaceutical compositions of the disclosure into capsules are also well-known in the art, and can comprise mixing the active ingredient and stabilizing polymer with one or more pharmaceutically acceptable capsule excipients and filling the mixture into a capsule. In one embodiment, a pharmaceutical formulation of the disclosure (with or without additional excipients) can be filled into a capsule, such as a hard gelatin capsule. The hard gelatin capsule can be of any appropriate size, for example size '0', '0EL', '3', '4' and the like. For example, in one embodiment a capsule of the disclosure having a dosage strength of 25 mg of the active ingredient can be filled into a hard gelatin capsule of size 4, where the target capsule fill weight can comprise 100 mg. In another embodiment, a capsule of the disclosure having a dosage strength of 100 mg of the active ingredient can be filled into a hard gelatin capsule of size 0el, where the target capsule fill weight can comprise 400 mg.

Exemplary tablet and capsule dosage forms of the disclosure and methods for manufacturing them are shown in the Examples below.

Also provided herein are kits comprising at least one dosage form of the disclosure, for example a tablet or capsule, and instructions for administering the at least one dosage form to a subject. The kit can also comprise packaging or a container housing the at least one dosage form of the disclosure, and can also comprise instructions on storage, administration, dosing or the like and/or an insert regarding the active ingredient. The kit can also comprise instructions for monitoring circulating levels of the active ingredient (or metabolites thereof) once administered, and optionally materials for performing such assays including, e.g., reagents, well plates, containers, markers or labels, and the like. Other suitable components to include in kits of the disclosure will be readily apparent to one of skill in the art, taking into consideration the desired indication, dosing regimen, storage conditions and route of administration.

The pharmaceutical compositions of the disclosure can formulated for administration as a single dose or as multiple doses for continuous or periodic discontinuous administration. For continuous administration, a kit can include the pharmaceutical compositions of the disclosure in individual unit dosage forms (e.g., tablet or capsule), and optionally instructions for administering the individual unit dosage forms, for example, more than once daily (for example, twice daily), daily, weekly, or monthly, for a predetermined length of time or as prescribed. When the pharmaceutical compositions of the disclosure are to be delivered periodically in a discontinuous fashion, a kit can include placebos during periods when the individual unit dosage forms are not delivered.

Suitable packages or containers are known in the art for holding and dispensing pharmaceutical agents for periodic oral use. In one embodiment, the package comprises indicators for each administration period. In another embodiment, the package comprises a labeled blister package, dial dispenser package, or bottle. The kits of the disclosure can also comprise a means for containing any type of packaging that houses the unit dosage forms, for example bottles or vials, which can (for example) be held in close confinement for commercial sale such as, e.g., injection or blow-molded plastic containers into which the bottles or vials are retained.

The pharmaceutical compositions, dosage forms and kits of the disclosure are useful in treating conditions which are associated with dysregulation of one or more of the RAS/RAF/MEK/ERK and PI3K/AKT/PTEN/mTOR pathways. In one embodiment, such a condition comprises a disease is associated with abnormal cellular proliferation. The term "abnormal cellular proliferation" refers to the uncontrolled growth of cells which are naturally present in a mammalian body. In one embodiment, a disease which is characterized by abnormal cellular proliferation is cancer, for example cancer of the prostate, head, neck, eye, mouth, throat, esophagus, bronchus, larynx, pharynx, chest, bone, lung, colon, rectum, stomach, bladder, uterus, cervix, breast, ovaries, vagina, testicles, skin, thyroid, blood, lymph nodes, kidney, liver, intestines, pancreas, brain, central nervous system, adrenal gland, skin or a leukemia or lymphoma. In one embodiment, the disease characterized by abnormal cellular proliferation is cancer of the prostate. In another embodiment, the abnormal cellular proliferation is associated with at least one solid tumor.

In another embodiment, a condition associated with dysregulation of one or more of the RAS/RAF/MEK/ERK and PI3K/AKT/PTEN/mTOR pathways comprises acute or chronic inflammatory disorders, such as neutrophil-associated inflammation, inflammatory arthritis, inflammation in peritonitis, inflammation after myocardial infarction or bleomycin-induced pulmonary fibrosis. Models for testing the ability of compounds to reduce inflammation in inflammatory arthritis are known, e.g., as described by Camps et al, Nature Med., 2005, 11, 936-943, which also describes models useful in assessing the ability of compounds to reduce inflammation in peritonitis; models for testing the ability of compounds to reduce inflammation and/or improve healing after myocardial infarction are described by Siragusa et al, Circ. Res. (2010), 106, 757-768; and a model for testing the ability of compounds to prevent bleomycin-induced pulmonary fibrosis is described by Wei et al, Biochem Biophys Res Comm. 2010, 397: 311-317 and Brent et al, Toxicology, 2000, 147: 1-13, the entire disclosures of which are incorporated herein by reference.

The disclosure thus provides a method of treating a disease characterized by the dysregulation of one or both of the RAS/RAF/MEK/ERK and PI3K/AKT/PTEN/mTOR pathways in a subject, comprising administering to the subject a therapeutically effective amount of an active ingredient in one or more dosage forms, wherein the dosage forms comprise a pharmaceutical formulation comprising an active ingredient in substantially amorphous form and one or more stabilizing polymers, wherein the active ingredient comprises a compound of the formula (I), and wherein the active ingredient remains in substantially amorphous form after storage of the pharmaceutical formulation for a predetermined time and under predetermined conditions.

As used herein, a therapeutically effective amount of an active ingredient of the disclosure when used for the treatment of cancer is, for example, an amount which may reduce the number of cancer cells in fluids (e.g., blood, peripheral cells or lymphatic fluids), reduce tumor size, inhibit metastasis, inhibit tumor growth and/or ameliorate one or more of the symptoms of the cancer. For cancer therapy, efficacy can be measured for example, by assessing the time to disease progression and/or determining the response rate.

As described herein, a therapeutically effective amount of an active ingredient of the disclosure when used for the treatment of an inflammatory disorder is an amount which may delay the onset of or reduce the severity or duration of an inflammatory response, or which mitigates one or more symptoms of an inflammatory response. For treatment of an inflammatory disorder, efficacy can be measured, for example, by a reduction in physiologic signs of inflammation (e.g., redness, swelling, heat, loss of function) or by measuring changes in the levels of cells (e.g., monocytes, macrophages and other mononuclear cells) or molecules (e.g., pro-inflammatory cytokines) associated with inflammation.

The RAS/RAF/MEK/ERK and/or PI3K/AKT/PTEN/mTOR pathways are known to be deregulated in various cancers due to specific mutations in different members of each pathway. For example, in RAS/RAF/MEK/ERK pathway, RAS protein is mutated frequently at residues 12, 13 and 61, while B-RAF is typically mutated only at amino acid position 600. The RAS gene mutations are easily detected in tumor samples using the methods known in the art, such as described by Sarkar et al (Diagn Mol Pathol. (1995) 4(4): 266-73), the entire disclosure of which is herein incorporated by reference, while B-RAF mutations can be detected for example with an FDA approved kit available from Roche (Cobas® 4800 BRAF V600 Mutation Test)

In the PI3K/AKT/PTEN/mTOR pathway, PI3K-alpha isozymes, PTEN and less frequently AKT are mutated in a wide variety of solid tumors. For example, the PI3K-alpha subunit is commonly mutated at residues 542, 545 and 1047. Similarly, mutations have been identified in PTEN tumor suppressor gene in a broad range of solid tumors, which cause the loss of PTEN activity through either frame-shift or non-sense mutations. About 3% of breast cancer tumors exhibit mutations in AKT protein at position 17.

Identifying a mammalian subject, e.g., a human patient, who will respond positively to treatment with pharmaceutical formulations of the disclosure prior to initiation of treatment (also termed herein "predetermining or selecting") can be accomplished by assaying a sample from a cancer patient to detect one or more of the RAS, B-RAF, PI3K isozymes, PTEN or AKT mutations discussed above.

A suitable sample may be obtained from the body of a subject and may include, e.g., tissue samples, cells, extracellular matter, circulating cancer cells in blood or lymphatic fluid. Tissue samples may be from any organ, including disease states of such organs, the blood circulatory system, and any circulating tumor cells. Tissue samples such as tumor biopsies may be obtained using known procedures. Tissue specimens may also include xenograft tumor samples, e.g., those from animals used in drug dose or toxicology studies.

For example, a subject can be tested for the presence of a B-RAF mutation and an mTOR mutation, for a B-RAF mutation and a PI3K mutation, or for a B-RAF mutation, an mTOR and a PI3K pathway mutation. As discussed above, these mutations can be detected using any suitable technique known in the art, including fluorescence in situ hybridization, PCR-based sequencing of relevant portions of a given gene, restriction fragment length polymorphism analysis, or by monitoring expression levels of a given gene product (e.g., protein or RNA). B-RAF, mTOR and PI3K mutations can also be detected by measuring activity of biomarkers in the RAS/RAF/MEK/ERK and/or PI3K/AKT/PTEN/mTOR pathways. Thus, there is provided a method for treating a condition treatable by inhibiting the RAS/RAF/MEK/ERK and PI3K/AKT/PTEN/mTOR pathways, comprising selecting a subject who has a B-RAF, PI3K and/or PTEN mutation; and administering a therapeutically effective amount of a pharmaceutical formulation of the disclosure.

The therapeutically effective amount of a pharmaceutical formulation of the disclosure provided to a subject will vary depending upon the purpose of the administration, the state of the patient, level of disease penetration and the like. As used herein, "subject" includes any human or non-human animal in need of treatment with the pharmaceutical formulations of the disclosure. In one embodiment, a subject is any human in need of treatment with the formulations of the disclosure (sometimes referred to herein as a "patient"). A therapeutically effective amount of the active ingredient in the pharmaceutical formulations of the disclosure can be determined by an ordinarily skilled physician or medical professional, taking into account certain variables, including the specific condition and the size, age, weight, gender, disease penetration, previous treatment and response pattern of the patient.

In one embodiment, the pharmaceutical formulation is administered orally in capsule or tablet form. For example, the present formulations can be provided as a unit dose, for example as a capsule, which taken together comprise a therapeutically effective amount. In one embodiment, a unit dose comprising the pharmaceutical formulation of the disclosure can be administered once daily or multiple times daily, for example, 1 to 6 times in a 12 or 24 hour period. If multiple unit doses are administered in a given time period, they can be administered at substantially even time intervals. For example, if two unit doses are administered in a 12 hour period, they can be given to the patient 6 hours apart. Multiple unit doses are administered in a given time period can also be administered at substantially uneven time intervals. In one embodiment, a unit dose comprises a dosage form of the disclosure in the form of a tablet or capsule for oral administration. In one embodiment, a unit dose is administered once in a 24 hour period (for example, "quaque die" or "QD" administration). In another embodiment, a unit dose is administered twice in a 24 hour period (for example, "bis in die" or "BID" administration.)

A suitable daily or twice daily (i.e., 24 hour time period) dose according to methods of the disclosure, whether given all at once or in multiple administrations, can depend on the specific method of treatment and condition treated. In one embodiment, a suitable daily dose, whether given all at once or in multiple administrations, is between about 10 to 1500 mg for oral application, for example about 20 to 500 mg, 50 mg to 250 mg or 75 mg to 100 mg. In other embodiments, a suitable daily dose is about 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 120 mg, 160 mg, 200 mg, 240 mg, 250 mg, 300 mg, 400 mg, 500 mg, 600 mg, 700 mg, 800 mg, 900 mg, 1000 mg, 1100 mg, 1200 mg, 1300 mg, 1400 mg or 1500 mg. In some embodiments, a suitable daily dose is about 10 mg, 20 mg, 40 mg, 120 mg, 240 or 400 mg. In one embodiment, a suitable twice daily dose is between about 800 to 1500 mg total dose for oral application, for example about 400 mg, 600 mg or 720 mg given twice daily (i.e., at each administration) for total doses of about 800 mg, 1200 mg or 1440 mg, respectively.

In another embodiment, a suitable daily or twice daily dose, whether given all at once or in multiple administrations, is about 0.1 mg/kg to about 100 mg/kg, about 0.5 mg/kg to about 75 mg/kg, about 0.1 mg/kg, 1 mg/kg, 10 mg/kg, 20 mg/kg, 50 mg/kg, 75 mg/kg or 100 mg/kg.

The pharmaceutical formulations of the disclosure can be administered with other therapeutics, for example oncology agents such as—(without limitation) dabrafenib, MEK inhibitors (for example, trametinib, binimetinib, cobimetinib, selumetinib, pimasertib), ERK inhibitors (for example, MK-8353, ulixertinib (BVD-523), GDC-0994, ASTX029), EGFR inhibitors (for example, gefitinib, erlotinib, osimertinib, dacomitinib, afatinib, cetuximab, panitumumab), pictilisib, vemurafenib, dasatinib, imatinib, panobinostat, palbociclib, ribiciclib, abemaciclib, olaparib, rucaparib, ibrutinib, crizotinib, alectinib, idelalisib, trastuzumab, cetuximab, other anticancer agents (for example, targeted agents, chemotherapy and immunotherapies), anticancer hormonal therapies (for example, tamoxifen, anastrozole, letrozole, exemestane, fulverstrant), anticancer GnRH analosgues (for example, goserelin, leuprolide), or anti-PD-1 antibodies.

The following examples are given to illustrate exemplary embodiments of the present disclosure. It should be understood, however, that the present disclosure is not to be limited to the specific conditions or details described in these examples.

EXAMPLES

Example 1—Hygroscopic Properties of Unstabilized N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide The hygroscopic properties of an active ingredient of the disclosure was shown by exposing N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide to increasing relative humidity (from 0% to 95%) at 25 degrees Celsius over 3200 minutes, and measuring the weight change of the active ingredient. The results are shown in Table 2 and FIG. 1, which demonstrates that the weight of the active ingredient increases in direct proportion to the increasing relative humidity, indicating that it is hygroscopic and can exist as variable hydrate depending on the humidity.

TABLE 2

| Time min | Temperature ° C. | Relative Humidity % | Weight Change % |
| --- | --- | --- | --- |
| 299.93 | 25 | 0 | 0.00001911 |
| 630.76 | 25 | 10 | 0.3832 |
| 750.76 | 25 | 20 | 0.5299 |
| 1190.76 | 25 | 30 | 1.087 |
| 1790.77 | 25 | 40 | 1.782 |
| 2390.77 | 25 | 50 | 2.661 |
| 2880.77 | 25 | 60 | 3.26 |
| 3010.78 | 25 | 70 | 3.407 |
| 3120.78 | 25 | 80 | 3.533 |
| 3200.79 | 25 | 90 | 3.635 |
|  |  | 100 |  |

Figure 2:
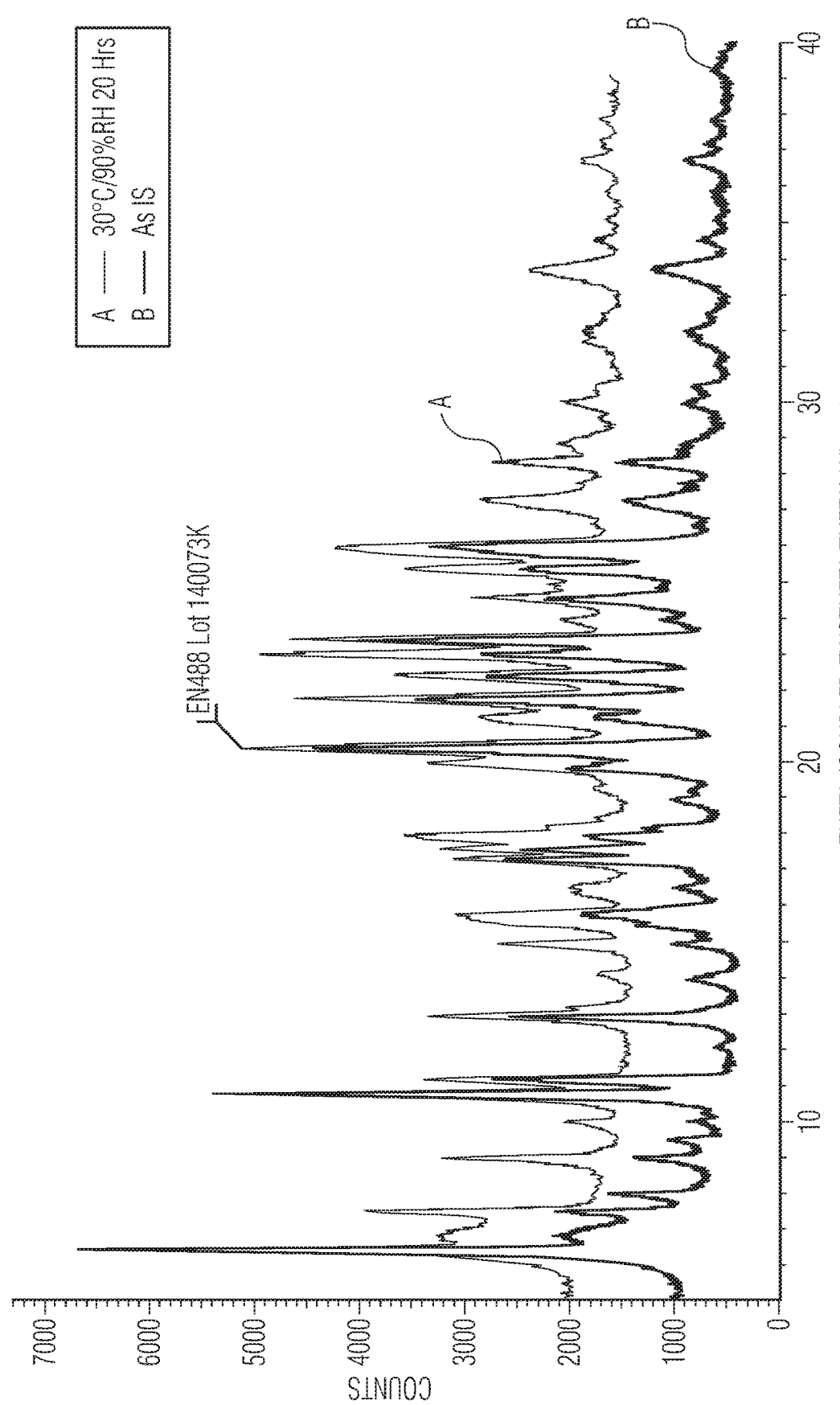
FIG. 2 is an X-ray powder diffraction (XRPD) spectrum showing the potential polymorphism or hydration state of unstabilized active ingredient N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide exposed to 30 degrees Celsius and 90% relative humidity for 20 hours. "As-Is"—active ingredient prior to exposure. "30° C./90% RH 20 Hrs"—active ingredient after exposure.

FIG. 2 shows the potential polymorphism or hydration state of the unstabilized active ingredient after being exposed to 90% relative humidity at 30 degrees Celsius for 20 hours. The physical state was measured by X-ray powder diffraction (XRPD).

An exemplary protocol for the XRPD method is as follows. In an embodiment, the exemplary protocol is used in all examples described herein.

Experimental Conditions

Experimental conditions for the exemplary XRPD method are provided below in Table 8.

TABLE 8

| Experimental Settings for XRPD | |
| --- | --- |
| PARAMETERS | CONDITIONS USED |
| Instrument: | Bruker D8 Advance |
| Radiation: | Cu Kα (Wavelength = 1.54 Å) |
| Mode: | Locked Coupled |
| Geometry: | Bragg-Brentano |
| Voltage: | 40 kV |
| Current: | 40 mA |
| Scan Mode: | Continuous |
| Divergence Slit: | 0.2 mm |
| Scan Range: | 2.0 to 40.0° 2θ |
| Step Size: | 0.00732° |
| Time/Step: | 0.3 s |
| Rotation: | 30 rpm |
| Sample Holder: | Poly (Methyl Methacrylate) (PMMA) sample cup |

Note:
Other parameters may be substituted as long as peak positions of the pattern are not compromised.

Sample Preparation

A powdered sample can be used for XRPD. The powder can be obtained by grinding tablets in a mortar with a pestle. The sample is placed into the large cavity of the PMMA sample holder. The surface of the sample is leveled, for example with a spatula, to produce a smooth surface along the lip of the cavity. Excess powder can be discarded.

Procedure

Instrument alignment verification can be performed, for example by running verification with Corundum Reference Standard according to the current version of SOP KQC-042, prior to sample analysis. After sample preparation, the sample is loaded into a multi-sample holder and the XRPD pattern is acquired with the parameters provided in Table 7. The pattern is processed with appropriate software, for example the Diffract Suite EVA software.

Data Analysis

Figure 19:
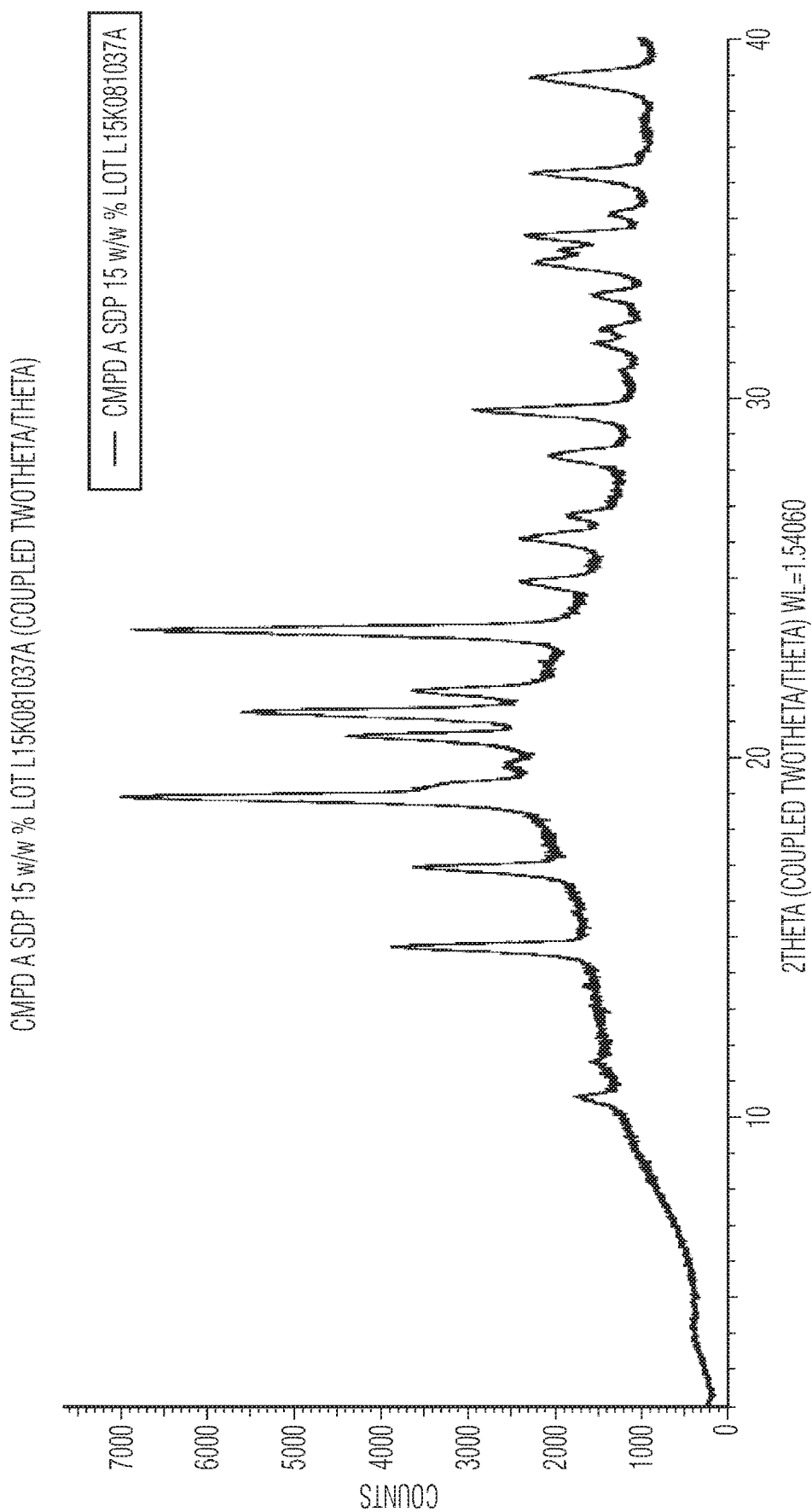
FIG. 19 shows an XRPD Reference Pattern for an active ingredient according to the present disclosure in spray granulated powder form.

Data analysis for the XRPD pattern can be performed as follows. The sample pattern is visually matched with an established reference pattern. All additional peaks corresponding to crystalline compound (e.g., crystalline active ingredient described herein) not detected in the reference pattern is reported. For example, XRPD reference patterns for the active ingredient described herein are provided below and also shown in FIGS. 19-22:

XRPD Reference Pattern for active ingredient in spray granulated powder form as shown in FIG. 19.

Figure 20:
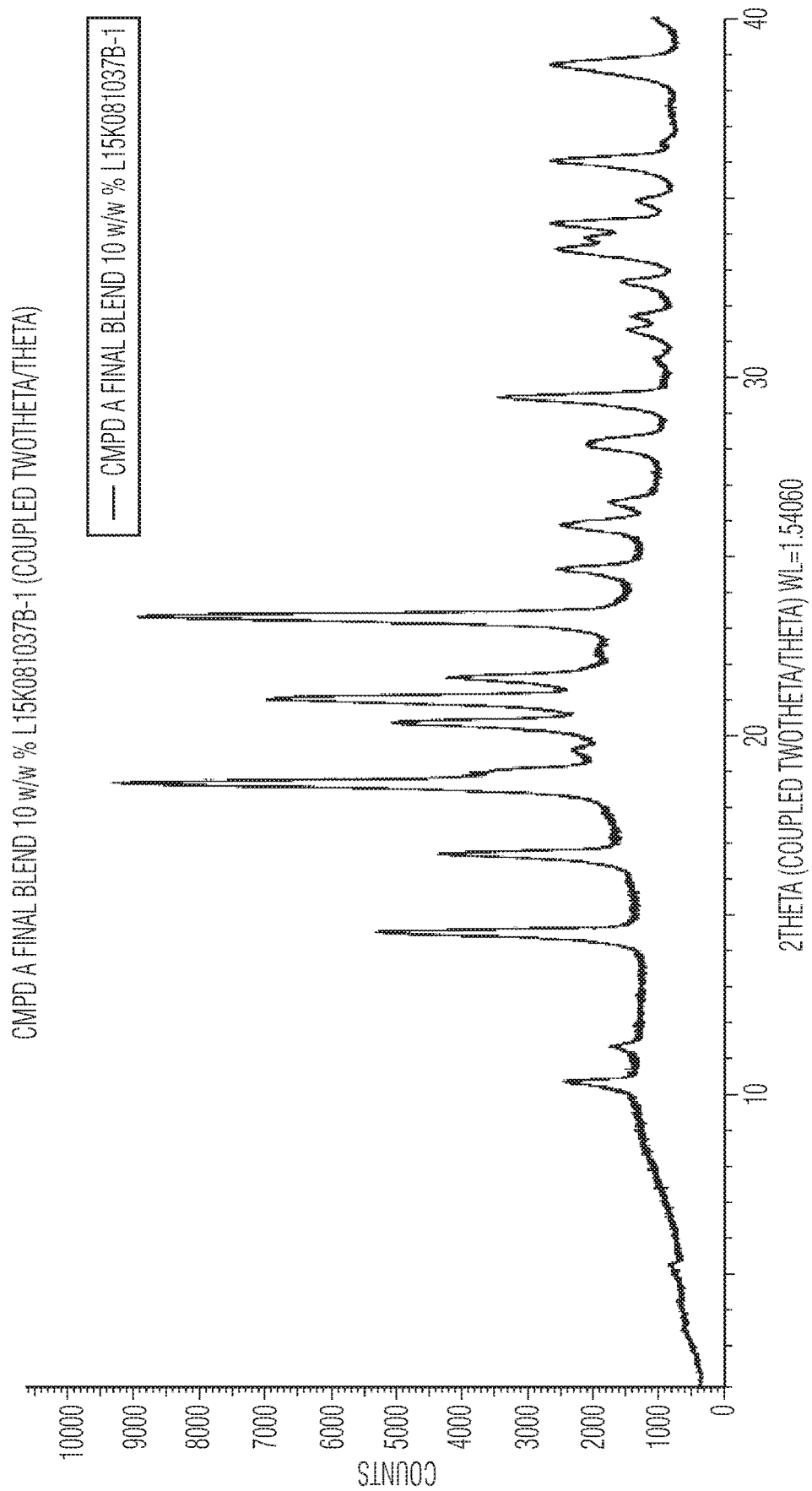
FIG. 20 shows an XRPD Reference Pattern for an active ingredient according to the present disclosure in spray granulated final blend form.

XRPD Reference Pattern for active ingredient in spray granulated final blend form as shown in FIG. 20.

Figure 21:
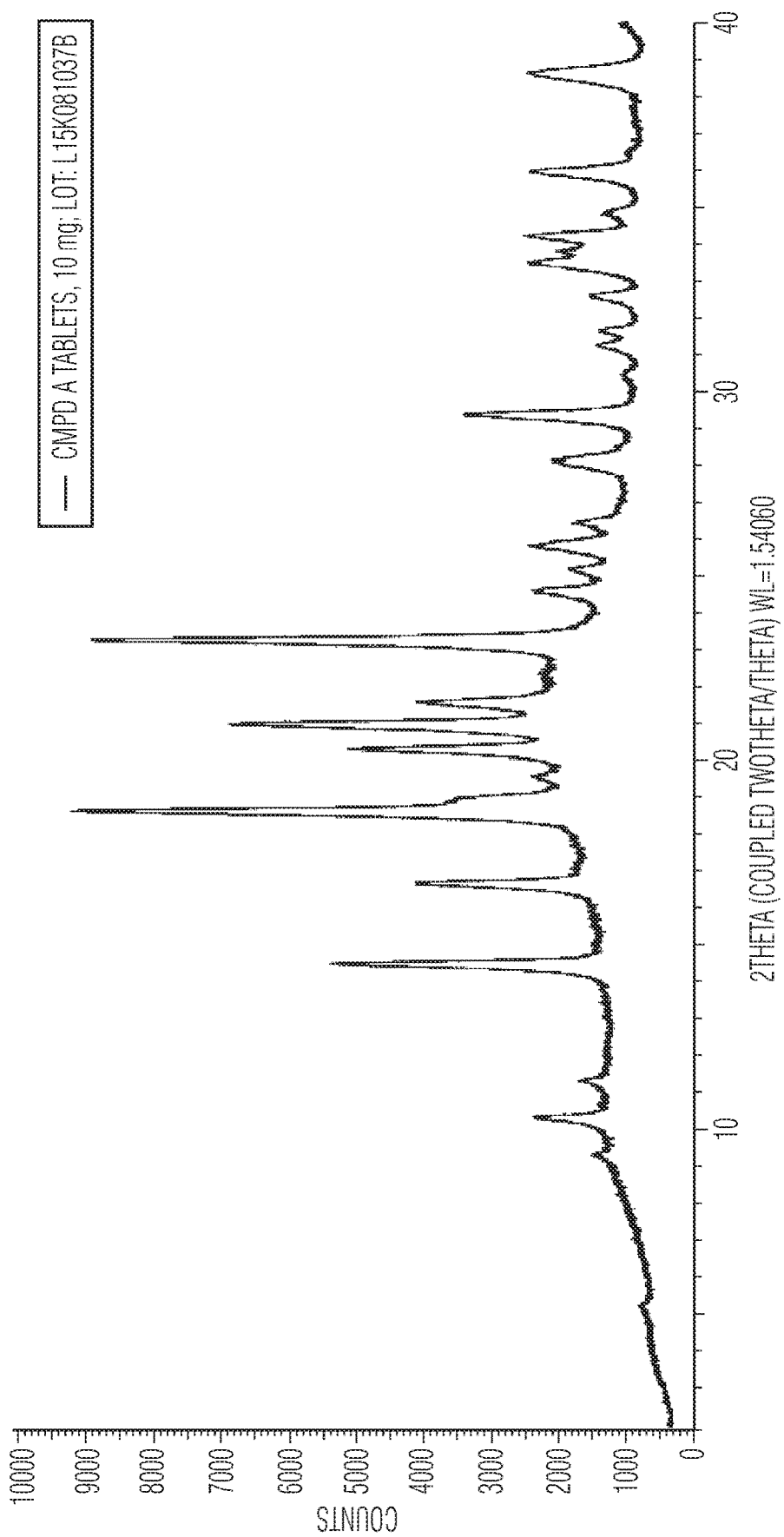
FIG. 21 shows an XRPD Reference Pattern for an active ingredient according to the present disclosure in 10 mg tablet form.

XRPD Reference Pattern for active ingredient in 10 mg tablet form as shown in FIG. 21.

Figure 22:
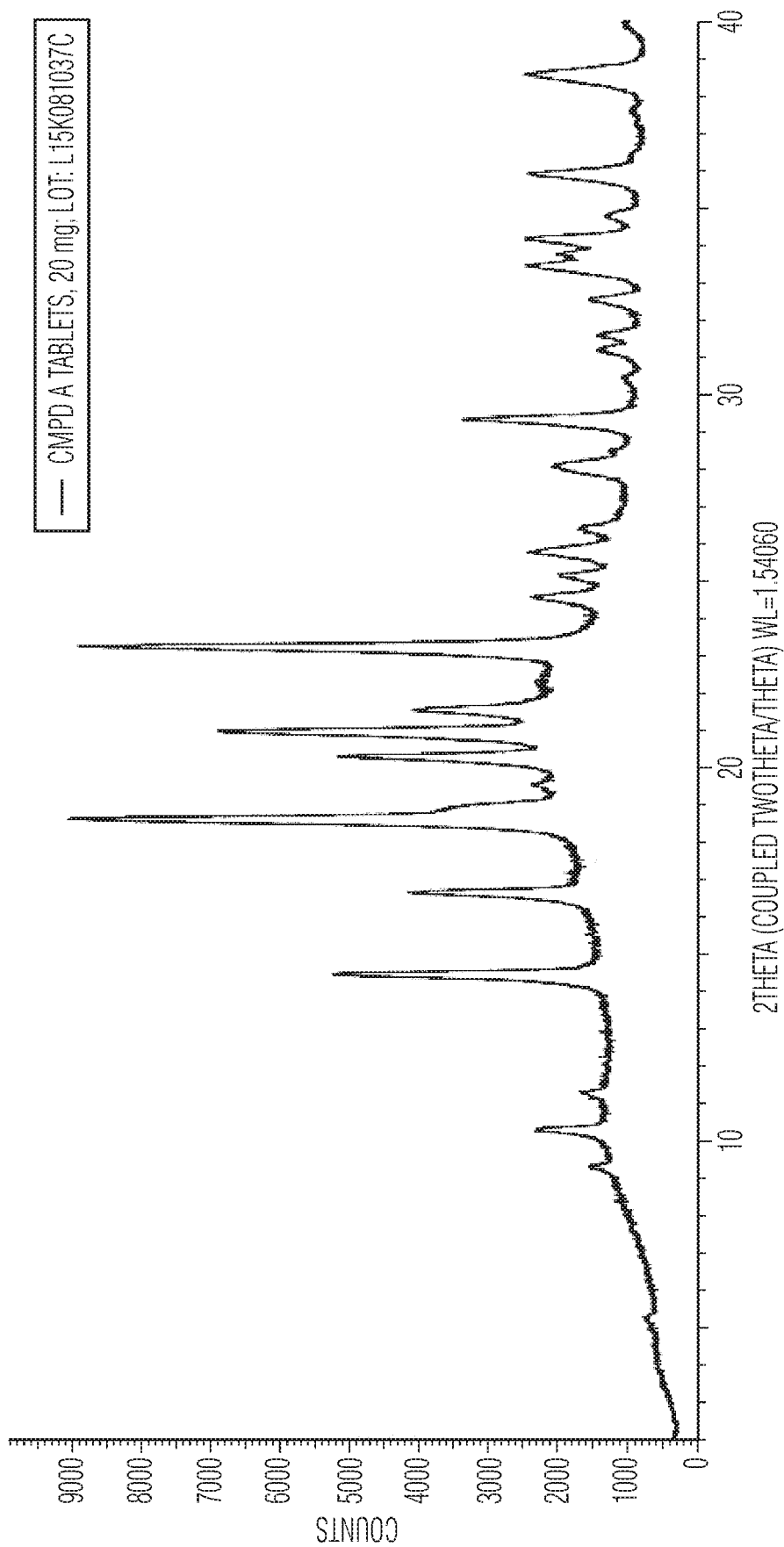
FIG. 22. shows an XRPD Reference Pattern for an active ingredient according to the present disclosure in 20 mg tablet form.

XRPD Reference Pattern for active ingredient in 20 mg tablet form as shown in FIG. 22.

Reporting

Results can be reported as "conforms" if: (a) the XRPD pattern of the sample visually matches the XRD pattern of the established reference pattern; and/or (b) no additional peaks corresponding to crystalline compound (e.g., crystalline active ingredient described herein) were detected.

Example 2—Effect of Stabilizing Polymers on N-(3-(2-(6-amino-4-(trifluoromethyl)pyridin-3-yl)-4-morpholinopyrido[3,2-d]pyrimidin-6-yl)-2-fluoro-phenyl)-3-fluoropropane-1-sulfonamide The ability of stabilizing polymers of the disclosure to maintain the active ingredient N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide in amorphous form was demonstrated by manufacturing a spray-dried formulation of 25% active ingredient and 75% HPMC-AS, Grade AS-L and a hot-melt extruded formulation of 24% w/w of the active ingredient, 72.5% w/w copovidone and 3.5% colloidal silicon dioxide powder, and exposing these formulations to various physical conditions.

The spray-dried formulation was made by dissolving 25% w/w of a crystalline form of the active ingredient (produced by the method of Example 7 below) in an excess of acetone, filtering this first solution to remove any particulates, and then dissolving 75% w/w HPMC-AS, grade AS-L in the first solution to make a second solution, and filtering the second solution to remove any particulates. The clarified second solution was spray dried on a Buchi 290 Mini Spray Dryer (Buchi Corp., New Castle, Del.) under the following conditions:

$T_{inlet}$=65 degrees Celsius

Exhaust Temperature, ~45-47 degrees Celsius

Air pressure, ~50 psi

Air flow, ~95 m3/hr

Spray rate, ~300 g/hr

Filter pressure, 50-80 kPa

Scale, ~100 g

The yield of spray-dried particles was approximately 60%, and the particles were subject to a secondary drying until the residual acetone solvent was below 1.5%. Particle size ranged from approximately 0.15 to 100 microns, with an average size of approximately 7 microns as measured on a Mastersizer 2000 particle size analyzer (Malvern Instruments, Ltd., Malvern, Worcestershire, UK) according the manufacturer's instructions, using hexane as a dispersant. The spray-dried particles were stable after storage in closed glass bottles for up to 4 weeks at accelerated conditions, indicating that there is no appreciable degradation of the active ingredient in this formulation when stored under these conditions, and indicating the formulation stored at 5 degrees Celsius would be stable for at least 3 months. Results from the accelerated stability storage are shown in Table 3 below.

TABLE 3

| Time Point | Condition | Assay | Impurities |
|---|---|---|---|
| Initial |  | 94.9 | 2.341 |
| 1 wk | 25/60% RH | 96.9 | 2.51 |
| 2 wk | 25/60% RH | 97.5 | 2.217 |
| 4 wks | 25/60% RH | 99.8 | 2.235 |
| 1 wk | 40/75% RH | 98.1 | 2.487 |
| 2 wk | 40/75% RH | 96.9 | 2.253 |
| 4 wks | 40/75% RH | 98.1 | 2.285 |

The hot melt extruded formulation was manufactured by blending 24% w/w of the active ingredient with 72.5% w/w copovidone (Kollidone® VA64) and melt-extruding the blend at 170-175° C. at 130 rpm, using 12 mm Brabender extruder, and milling the cooled extrudate using Fitz mill fitted with Size 0 stainless screen and knives to an average particle size in the range of 20-100 μm and blending it with 3.5% colloidal silicon dioxide powder (Cab-O-Sil®) at room temperature.

Figure 3:
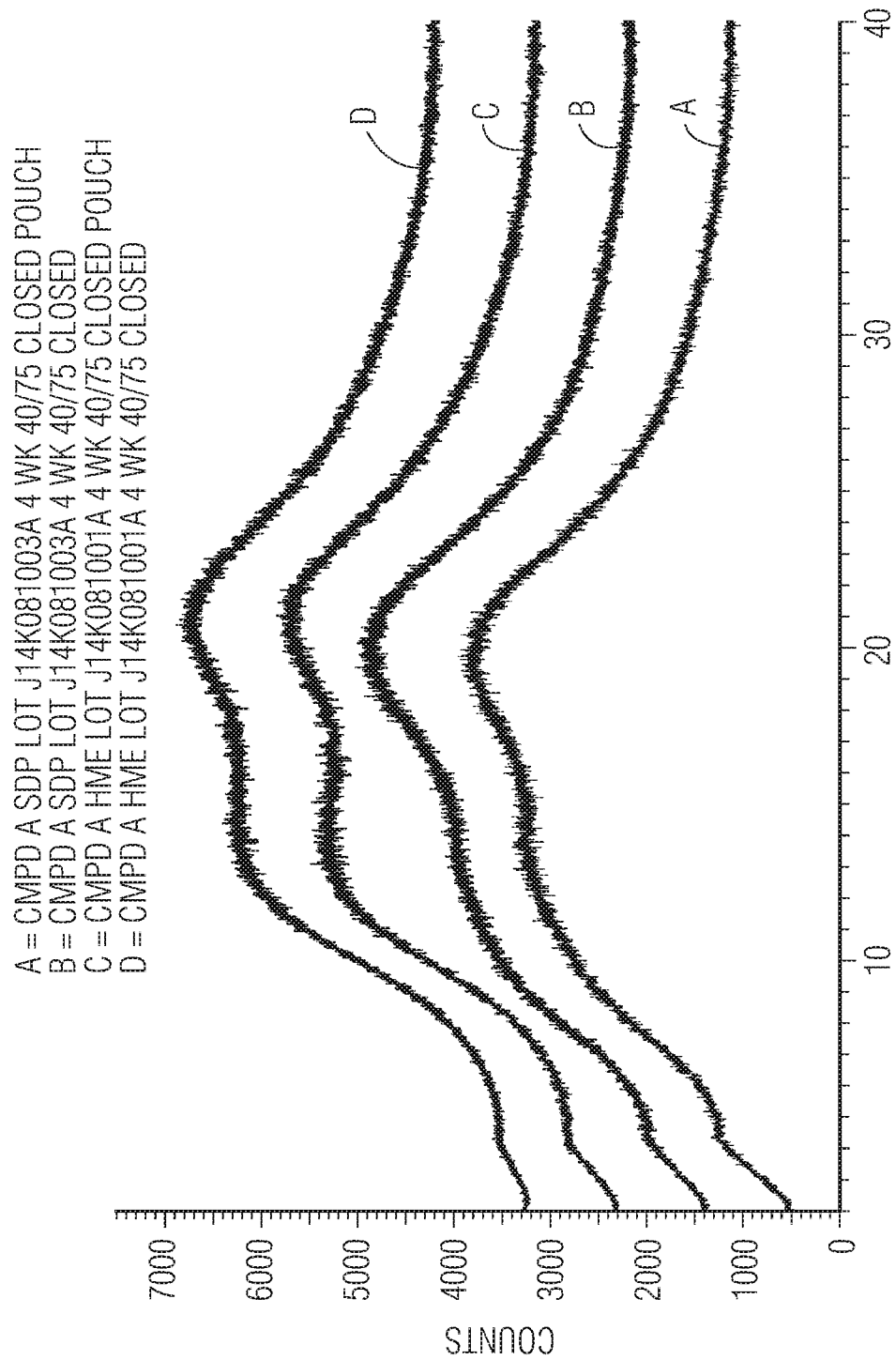
FIG. 3 is an XRPD spectrum showing the stability of particles of spray-dried and hot-melt extruded amorphous N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide and HPMC-AS (25:75) in a closed pouch or glass container over four weeks at 40 degrees Celsius and 75% relative humidity. "SDP" is spray-dried particles; "HME" is hot-melt extruded particles.

Analysis of the spray-dried and hot-melt extruded formulations stored in a closed pouch or glass container over four weeks at 40 degrees Celsius and 75% relative humidity by XRPD according to the methods described in Example 1 above demonstrated that the active ingredient in the particles remains in amorphous form throughout storage under these conditions (see FIG. 3).

Figure 4:
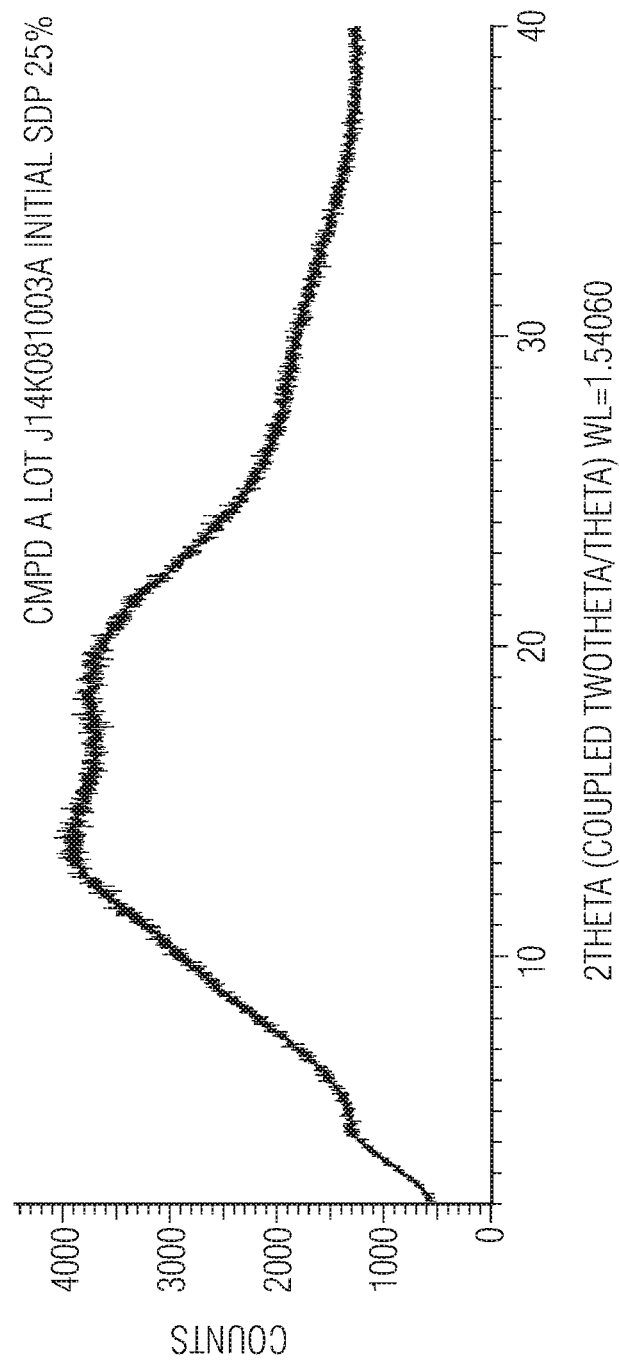
FIG. 4 is an XRPD spectrum showing the solution stability over four hours of particles of spray-dried amorphous N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide and HPMC-AS (25:75) dispersed in 0.2% HPC, 0.1% Tween 80.

The active ingredient in the spray-dried and hot melt extruded formulations also remained in amorphous form when dispersed in 0.2% hydroxypropyl cellulose and 0.1% Tween 80 for over four hours, as shown by XRPD analysis according to the methods described in Example 1 above (see FIG. 4).

Figure 5:
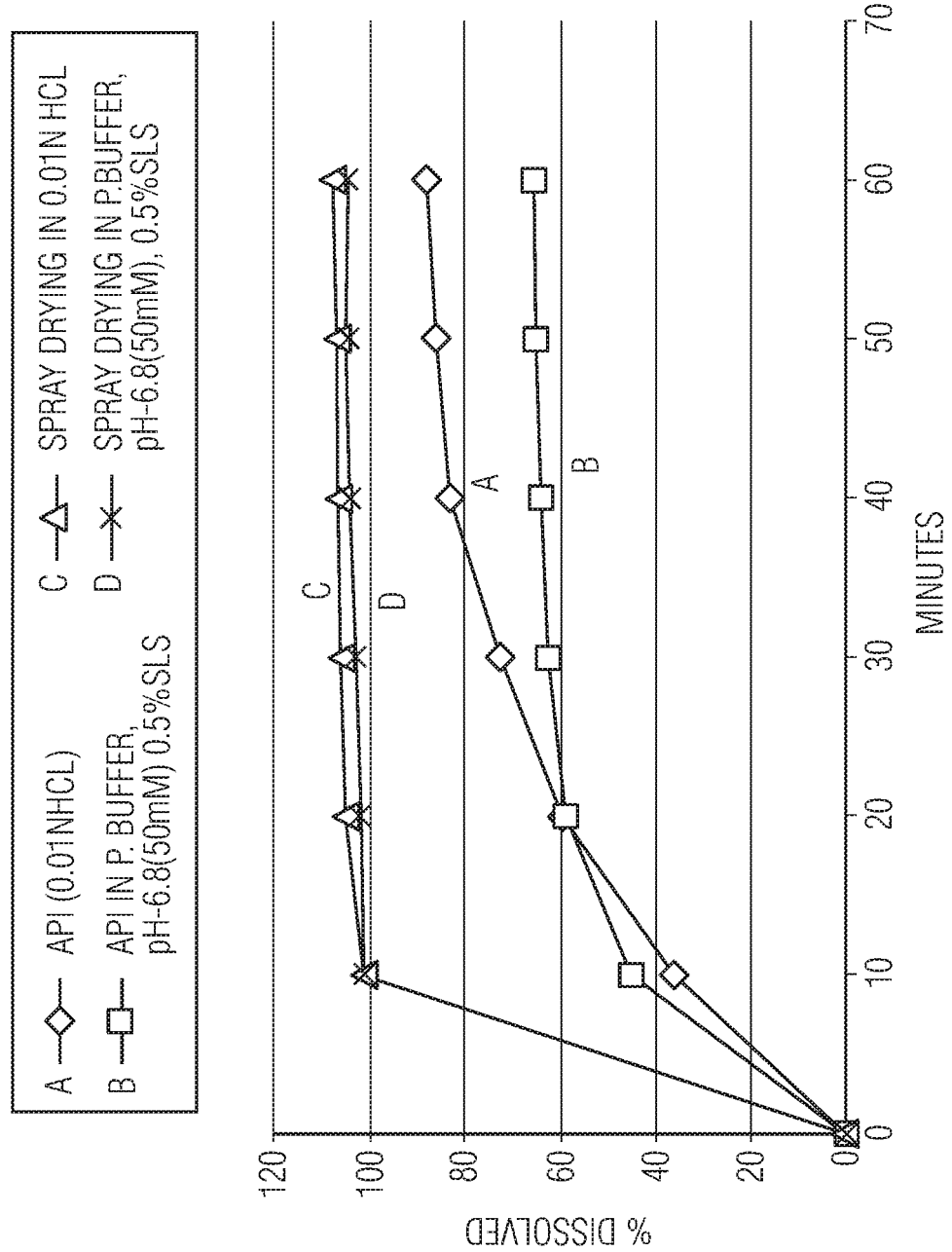
FIG. 5 is the dissolution profile of particles of N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide ("API") and spray-dried amorphous N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide and HPMC-AS (25:75) ("Spray Drying"). Dissolution was measured in 500 ml 0.01 N HCl or 50 mM phosphate buffer (pH 6.8), 0.5% sodium lauryl sulfate, by the paddle method at 50 rpm.

Example 3—Dissolution Characteristics of a Spray-Dried Formulation of N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide The dissolution characteristics of the spray-dried formulation prepared in Example 2 above were measured by suspending the formulation in 500 ml 0.01 N HCl or 50 mM phosphate buffer (pH 6.8), 0.5% sodium lauryl sulfate, and measuring dissolution by the USP <711> Apparatus 2 (paddle method) at 50 rpm. As a control, particles of crystalline active ingredient N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide (as prepared in Example 7 below) was suspended in either 500 ml 0.01 N HCl or 50 mM phosphate buffer (pH 6.8), 0.5% sodium lauryl sulfate and dissolution measured by the same method. Results of the dissolution studies are shown in FIG. 5, which indicates that 100% of the spray-dried formulation dissolved in approximately 10 minutes, while after 60 minutes the control particles were still not fully dissolved.

Example 4—Preparation of a Spray Granulated Formulation of N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide A spray granulated formulation of N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide for compression into 860 mg tablets containing 100 mg of the active ingredient was manufactured as described below, with the per-tablet ingredients as shown in Table 4 below.

TABLE 4

| Ingredient | mg/tablet |
|---|---|
| Intragranular | |
| Active Ingredient | 100.00 |
| Hypromellose Acetate Succinate, NF (Shin Etsu AQOAT, Grade: AS-LF) | 300.00 |
| Colloidal silicone dioxide (Cabosil M5P) | 10.00 |
| Mannitol, NF (Parteck M100) | 250.00 |
| Acetone, NF, EP | 10000.00* |
| Extragranular | |
| Crospovidone, NF, (Polyplasdone XL) | 40.00 |
| Microcrystalline cellulose, NF (Avicel PH101) | 30.00 |
| Mannitol, NF (Parteck M200) | 100.00 |
| Magnesium stearate, NF | 10.00 |
| Opdary II, White (85F18422) | 20.00 |
| Total | 860.00 |

*Removed during processing—not in final formulation.

Figure 6:
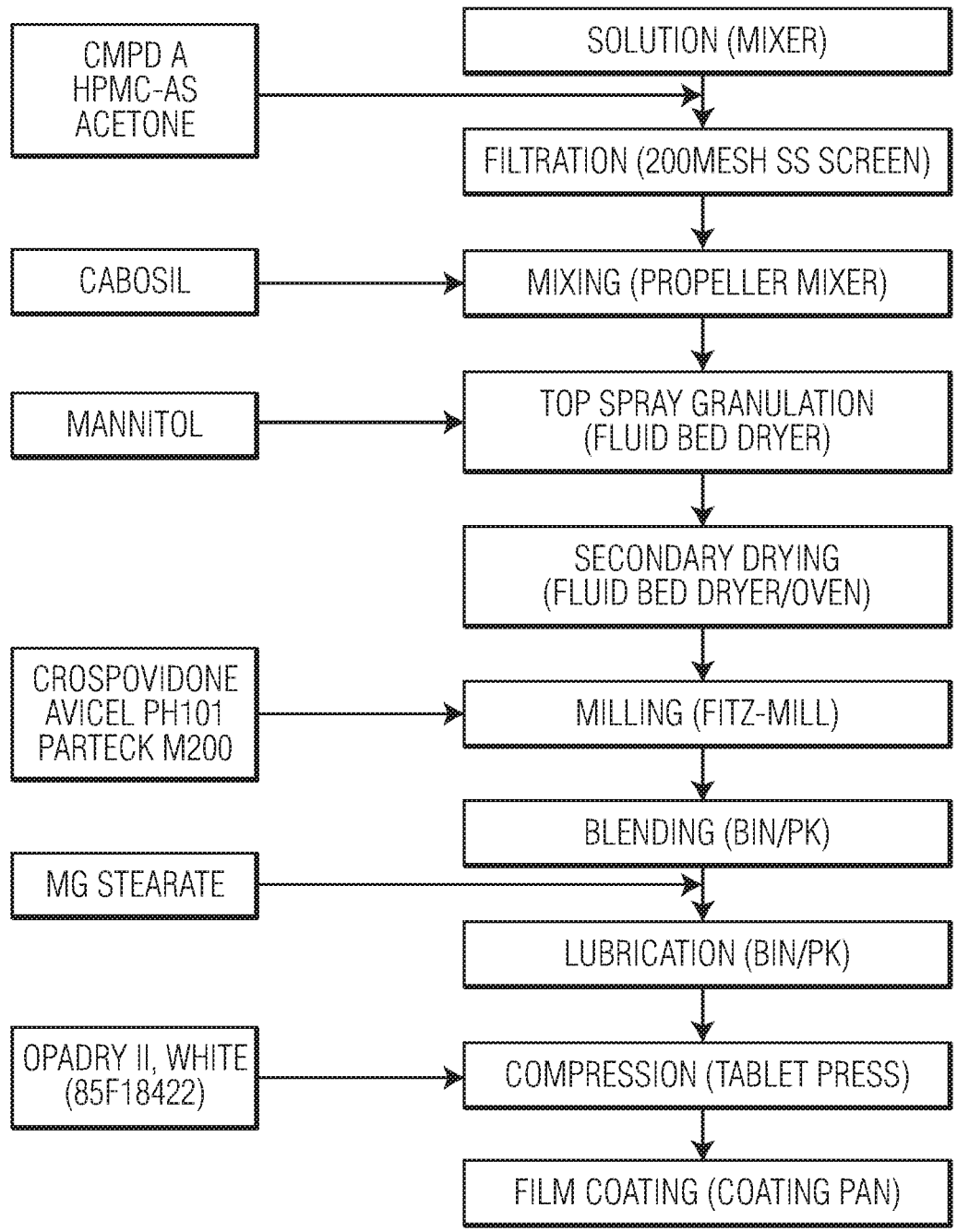
FIG. 6 is a flow diagram of an exemplary manufacturing process of the disclosure.

To make the formulation, crystalline active ingredient (as prepared in Example 7 below) and HPMC-AS, NF (Shin Etsu AQOAT, Grade: AS-LF) were dissolved in an excess of acetone (NF, EP) and filtered through a 200 mesh stainless steel screen. The colloidal silicone dioxide (Cabosil M5P) was added and the solution mixed with a propeller mixer and granulated in fluid bed dryer using top spray granulation method onto mannitol, NF (Parteck M100) while maintaining the exhaust temperature below 35° C. The dried spray granulated particles where then subject to secondary drying in a fluid bed dryer/oven at temperature below 35° C. until the residual solvent dropped below <0.5%, combined with the crospovidone, NF, (Polyplasdone XL) and microcrystalline cellulose, NF (Avicel PH101) and milled in a Fitz mill fitted with Screen #1512-0024 and knives forward at medium speed, and the milled particles blended in a 1 cf V-blender with the magnesium stearate, NF. This blend was combined with the extra-granular mannitol, NF (Parteck M200) and compressed into tablets with a Pressima tablet press. The tablets were then coated with x % Opadry II, white (85F18422) in a 15 inch Thomas coating pan (Thomas Engineering Inc., Hoffman Estates Ill.). A flow diagram of this procedure is shown in FIG. 6.

Figure 7:
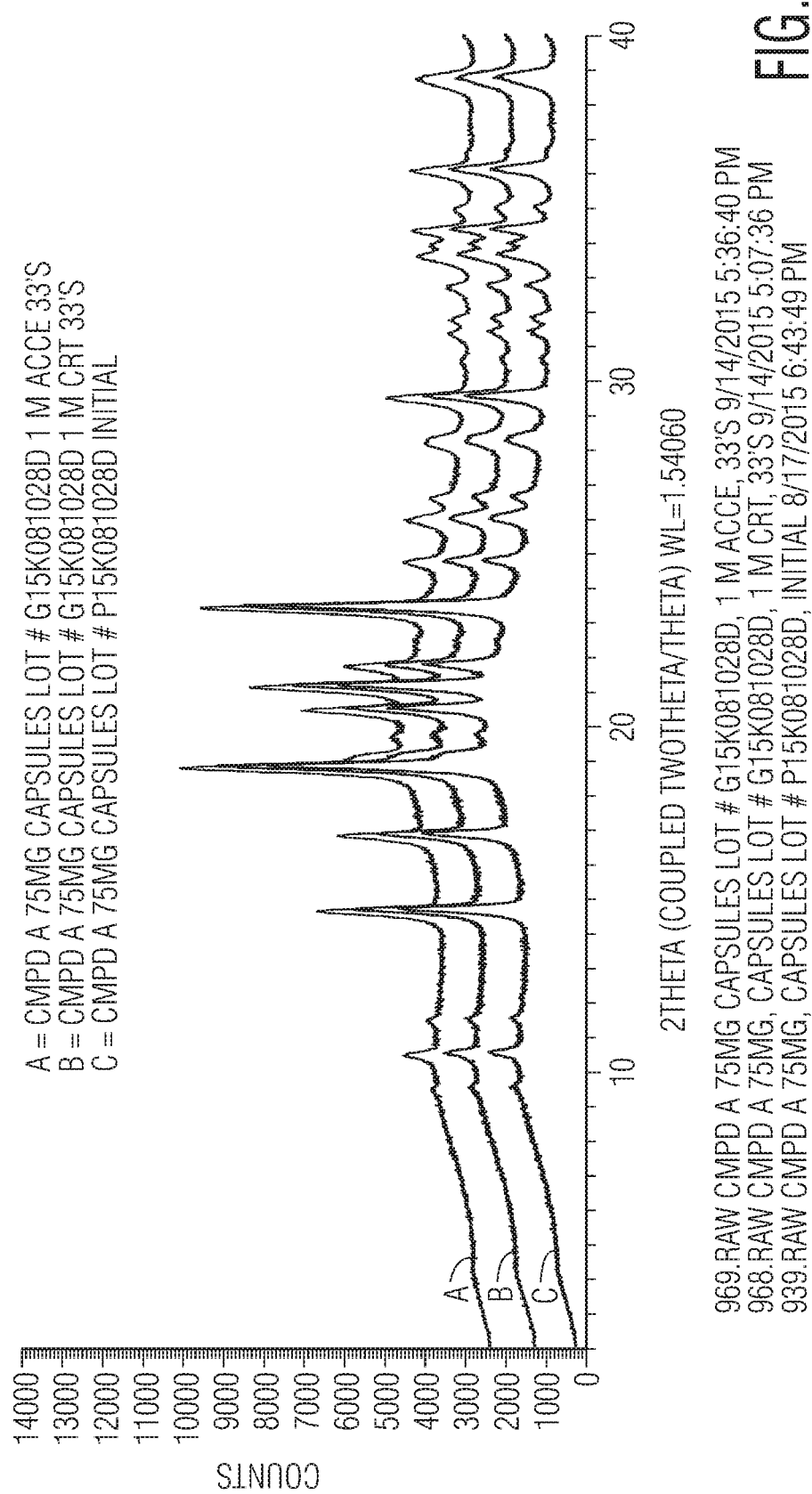
FIG. 7 is XRPD spectrum showing the stability of a pharmaceutical formulation of the disclosure in capsule form (75 mg active ingredient per capsule), measured upon manufacture, and after one month storage at 25 degrees Celsius/60% relative humidity ("ACC") and 40 degrees Celsius/75% relative humidity ("CRT").
Figure 8:
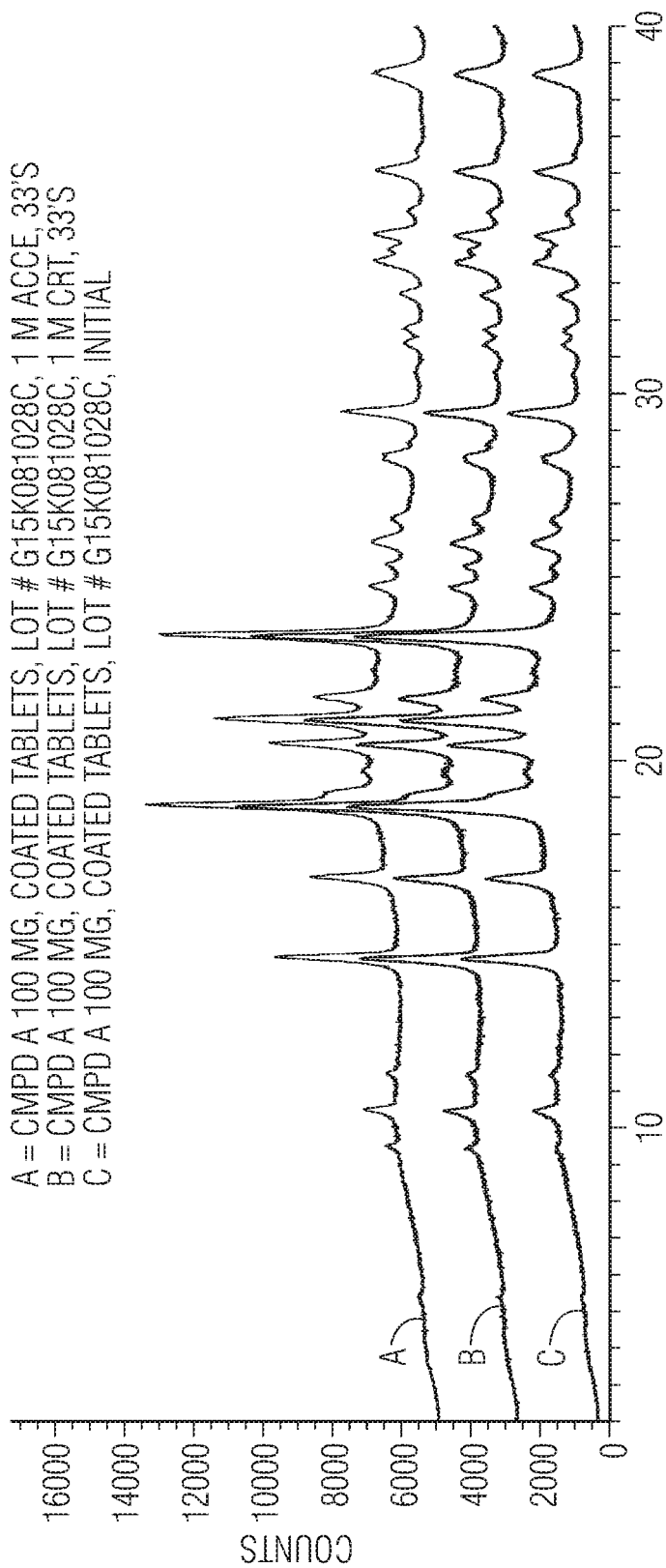
FIG. 8 is XRPD spectrum showing the stability of a pharmaceutical formulation of the disclosure in tablet form (100 mg active ingredient per capsule), measured upon manufacture, and after one month storage at 25 degrees Celsius/60% relative humidity ("ACC") and 40 degrees Celsius/75% relative humidity ("CRT").

For formation into capsules containing 75 mg of the active ingredient, the capsule formulation contained 0.25% Mg stearate as the extragranular excipient. The milled granules were blended with Mg stearate and were filled into opaque white hard gelatin capsules (Size 00) using a Dott. Bonapace & C. srl (Limbiate, Italy) In-Cap Bench-top Capsule Filler Stability of the active ingredient in both the capsule (FIG. 7) and tablet (FIG. 8) dosage forms was demonstrated by measuring the XRPD spectrum as described in Example 1 above upon manufacture and after storing them at 25 degrees Celsius and 60% relative humidity or 40 degrees Celsius and 75% relative humidity for one month. As shown in the figures, the active ingredient retains its amorphous after being subjected to the manufacturing procedure, and after storage for one month at the stated conditions.

Figure 9:
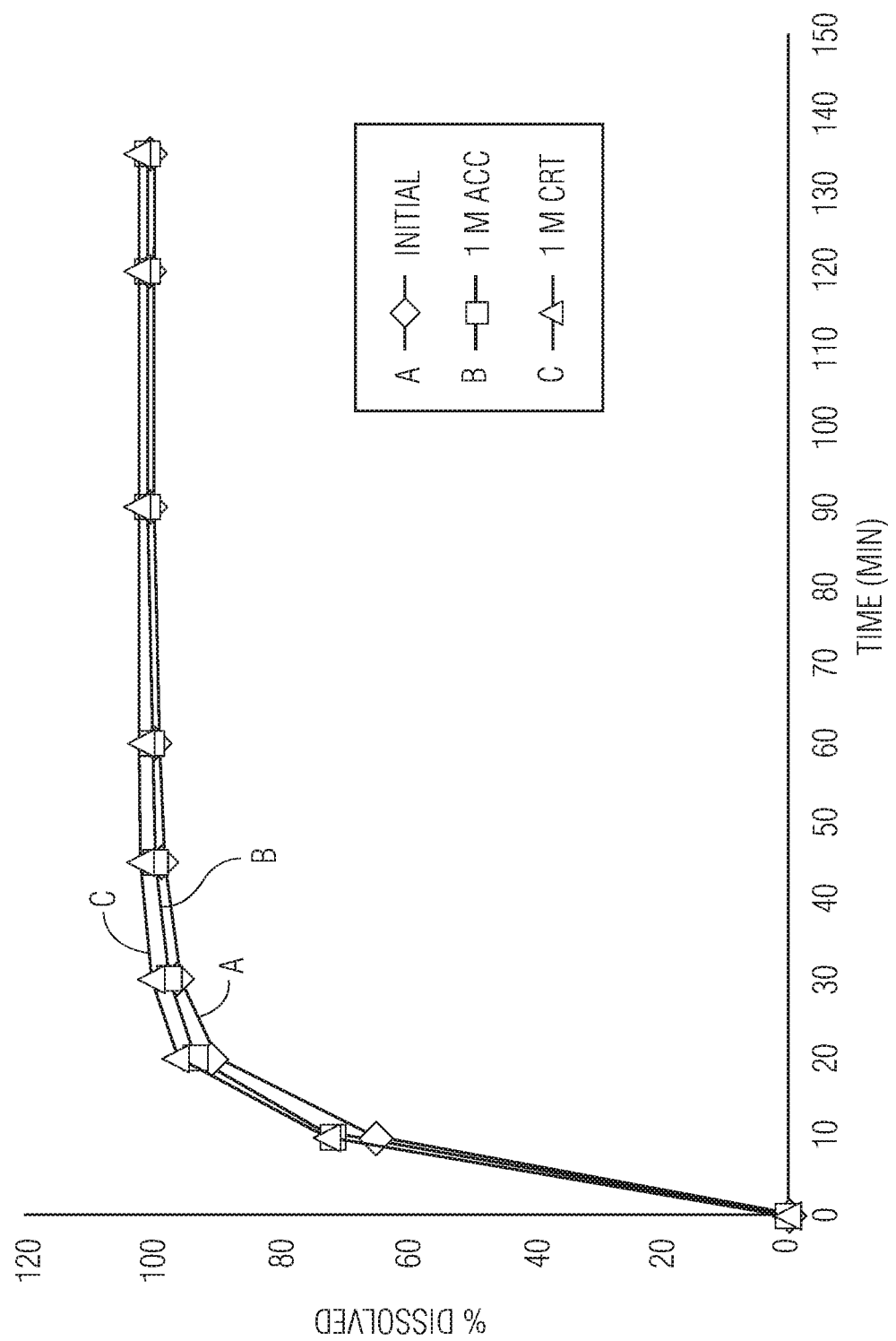
FIG. 9 is the dissolution profile of a pharmaceutical formulation of the disclosure in capsule form (75 mg active ingredient per capsule), measured in 900 ml of 10 mM phosphate buffer (pH 6.8), 2% sodium lauryl sulfate by the paddle method at 75 rpm upon manufacture, and after one month storage at 25 degrees Celsius/60% relative humidity ("ACC") and 40 degrees Celsius/75% relative humidity ("CRT").
Figure 10:
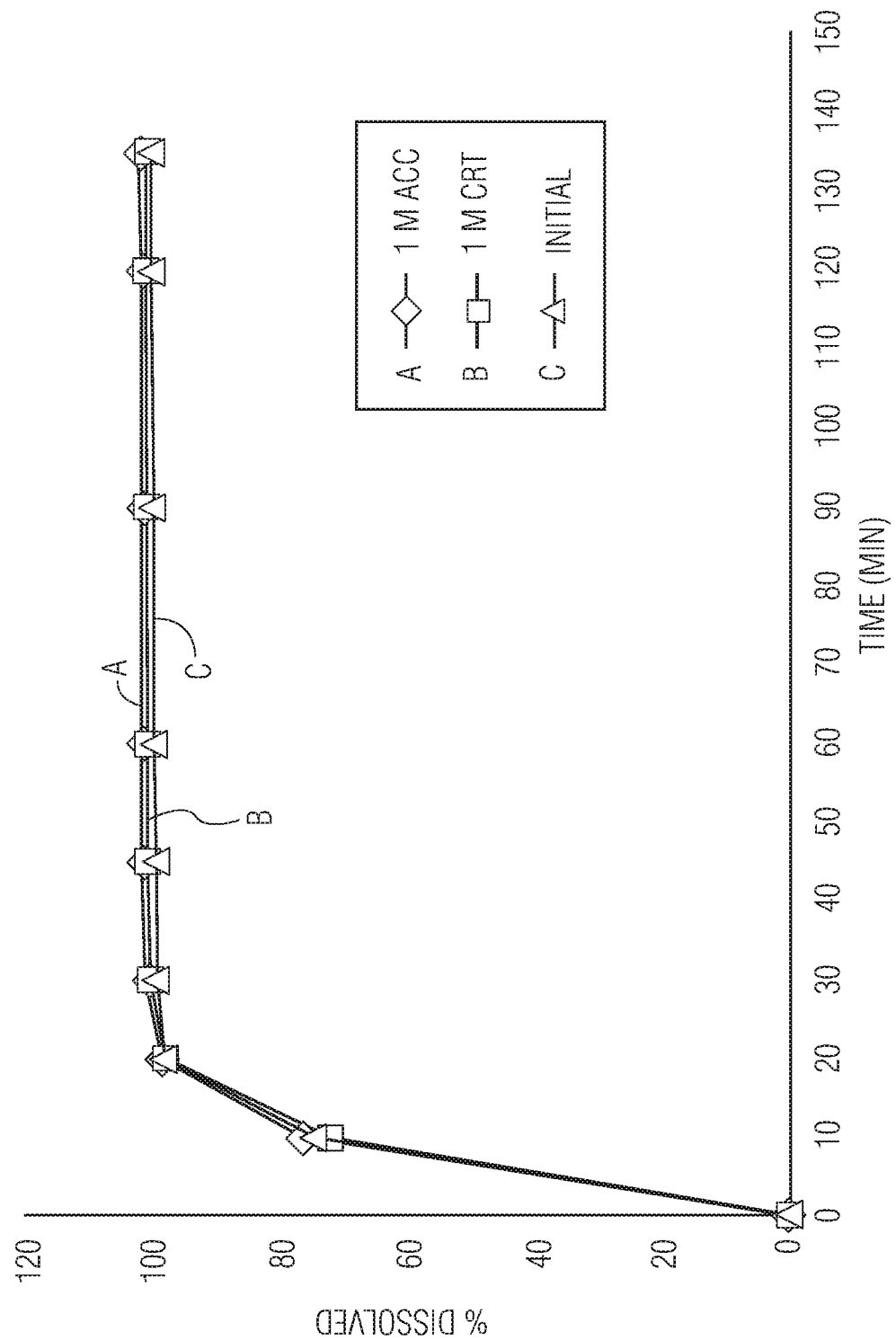
FIG. 10 is the dissolution profile of a pharmaceutical formulation of the disclosure in tablet form (100 mg active ingredient per capsule), measured in 900 ml of 10 mM phosphate buffer (pH 6.8), 2% sodium lauryl sulfate by the paddle method at 75 rpm upon manufacture, and after one month storage at 25 degrees Celsius/60% relative humidity ("ACC") and 40 degrees Celsius/75% relative humidity ("CRT").

Example 5—Dissolution Characteristics of a Spray-Granulated and Hot Melt Formulations of N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide The dissolution characteristics of the spray-granulated dosage forms as described in Example 4 above were measured by suspending the dosage forms in 900 ml of 10 mM phosphate buffer (pH 6.8), 2% sodium lauryl sulfate upon manufacture, and after one month storage at 25 degrees Celsius/60% relative humidity or 40 degrees Celsius/75% relative humidity, as determined by the USP Apparatus 2 <711> paddle method, at 75 rpm. As shown in FIG. 9 (capsules) and FIG. 10 (tablets), the dosage forms were 100% dissolved after about 20 minutes, as measured upon manufacture and after one month storage under the stated conditions.

Figure 11A:
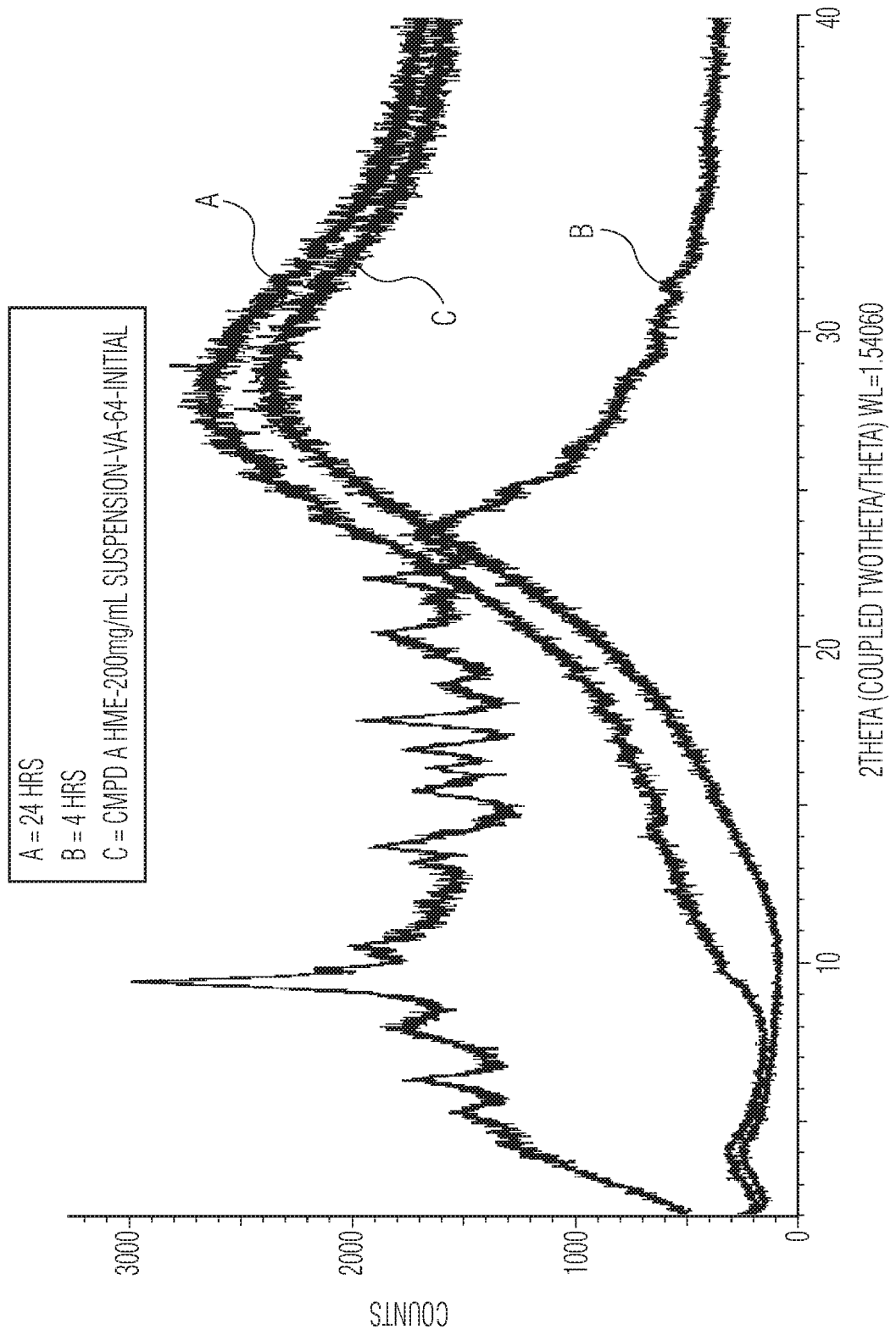
FIG. 11A is an XRPD spectrum showing the solution stability of particles of hot-melt extruded formulation of N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide with copovidone as stabilizing polymer but without colloidal silicone dioxide to provide stability in the suspension.
Figure 11B:
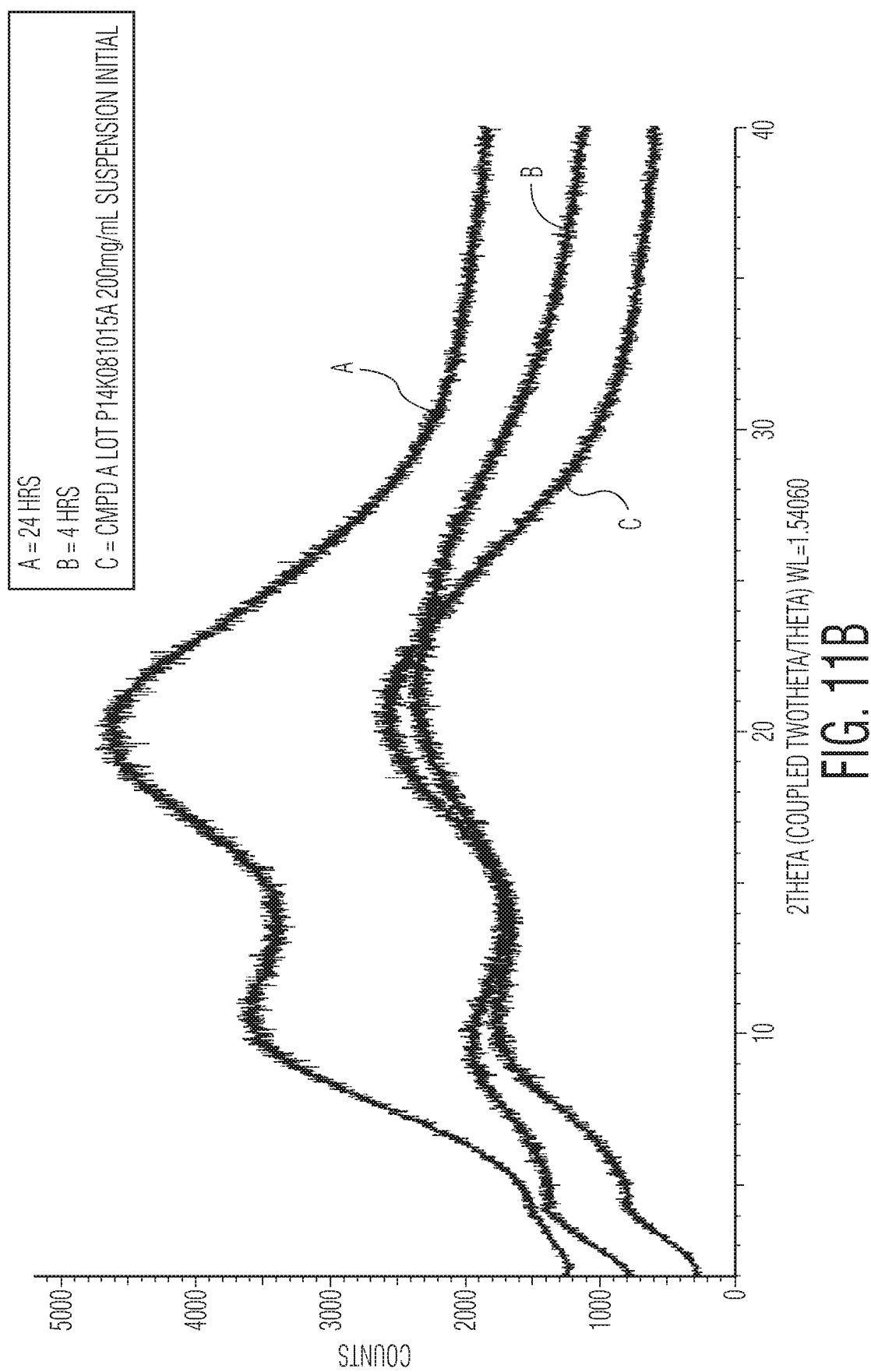
FIG. 11B is an XRPD spectrum showing the stability of particles of hot-melt extruded formulation of N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide with copovidone as stabilizing polymer and colloidal silicone dioxide as stabilizer for stability in the dispersed state. Both formulations were dispersed in 2% HPC, 0.1% Tween 80, and spectral analysis performed upon initial manufacture ("initial"), at 4 hours and at 24 hours.

The solution stability of particles of hot-melt extruded formulation of active ingredient N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide with (FIG. 11A) and without (FIG. 11B) copovidone stabilizing polymer was demonstrated by dispersing the formulations in 2.0 HPC, 0.1% Tween 80, and measuring the XRPD spectrum upon initial manufacturing, and at 4 hours and 24 hours after initial manufacturing. As shown in the figures, in the formulation without stabilizing polymer, the active ingredient migrates from amorphous form at the initial time point through crystal forms at 4 hours and back to amorphous form at 24 hours. In contrast, in the formulation with stabilizing polymer the active ingredient remains in the amorphous form through the 24 hours in suspension.

Example 6—Pharmacokinetic Characteristics of Spray-Granulated and Hot Melt Formulations of N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide in Animal Models The pharmacokinetic characteristics of formulations of the disclosure were demonstrated in both rats and dogs. In rats, a hot melt extrusion formulation (referred to as "Formula 2 in this Example 6) and a spray-dried formulation as prepared in Example X above ("Formula 3") prepared as described in Example 2 above were tested, along with a control formulation of the sodium salt of the active ingredient in 1% w/v copovidone, and 5% w/v TPGS in purified water, as a solution (Formulation 1). The formulations were administered to Sprague Dawley rats orally by gavage, and the results are shown in Table 5 below.

TABLE 5

PK Characteristics In Rats

| Dosage Form | Dose (mpk) | Male | | | | Female | | | |
|---|---|---|---|---|---|---|---|---|---|
| | | Cmax (ng/ml) | Tmax (hr) | $AU_{0-24}$ (ng/ml*hr) | Cl (ml/hr/kg) | Cmax (ng/ml) | Tmax (hr) | $AUC_{0-24}$ (ng/ml*hr) | Cl (ml/hr/kg) |
| Formulation 1 | 10 | 2753 | 2 | 28244 | 354 | 2435 | 2 | 29531 | 339 |
| Formulation 2 | 10 | 1161 | 4 | 19662 | 509 | 1070 | 8 | 19662 | 509 |
| | 30 | 3195 | 2 | 66723 | 450 | 3556 | 2 | 65419 | 459 |
| Formulation 3 | 10 | 5097 | 2 | 53743 | 186 | 2363 | 12 | 46533 | 215 |
| | 30 | 5355 | 12 | 108259 | 277 | 4802 | 12 | 103247 | 291 |

As can be seen from Table 5, the spray dried HPMC-AS formulation (Formulation 3) provided better exposures then the hot melt extruded formulation (Formulation 2), and both Formulations 2 and 3 provided better exposures that the control formulation (Formulation 1).

Formulations 1, 2 and 3 were administered orally to beagle dogs by gavage, and the results are shown in Table 6 below.

TABLE 6

PK Characteristics In Dogs

| Dosage Form | Dose (mg/kg) | Male | | | | Female | | | |
|---|---|---|---|---|---|---|---|---|---|
| | | Cmax (ng/ml) | Tmax (hr) | $AUC_{0-24}$ (ng/ml*hr) | Cl (ml/hr/kg) | Cmax (ng/ml) | Tmax (hr) | $AU_{0-24}$ (ng/ml*hr) | Cl (ml/hr/kg) |
| Formulation1 | | 1223 | 2 | 5809 | 2582 | 1331 | 2 | 6680 | 2245 |
| Formulation2 | 15 | 652 | 2 | 5232 | 2867 | 1024 | 2 | 5660 | 2650 |
| Formulation3 | | 821 | 0.5 | 5405 | 2775 | 1307 | 2 | 5710 | 2627 |

Figure 12A:
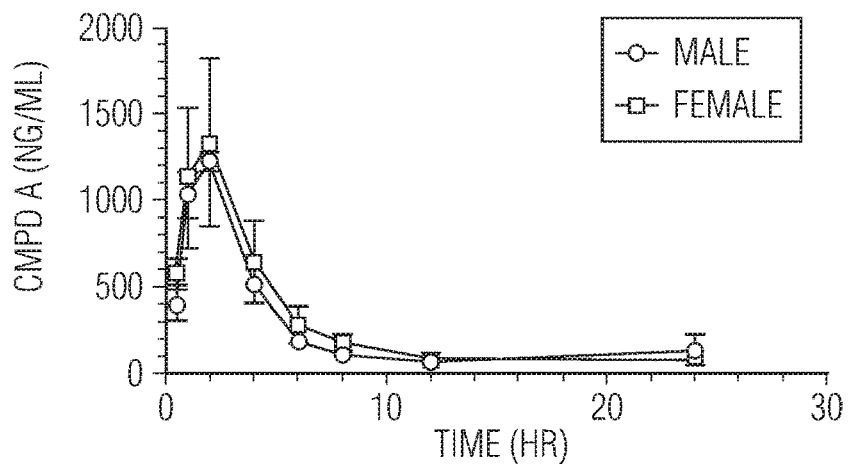
Figure 12B:
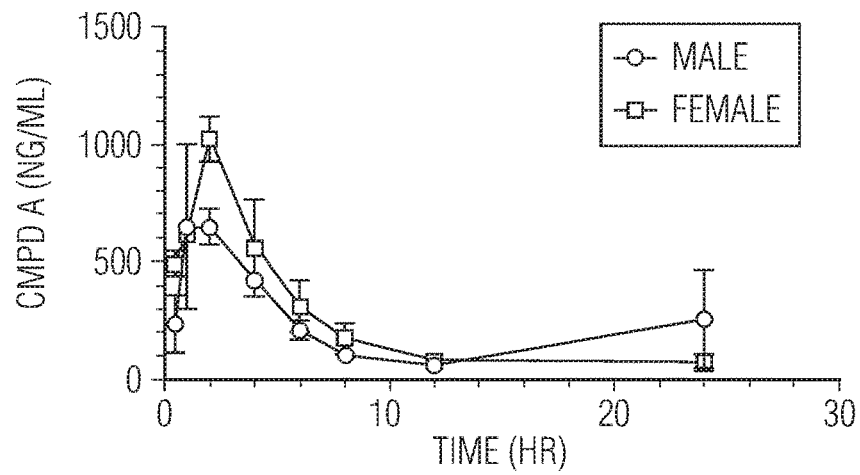
Figure 12C:
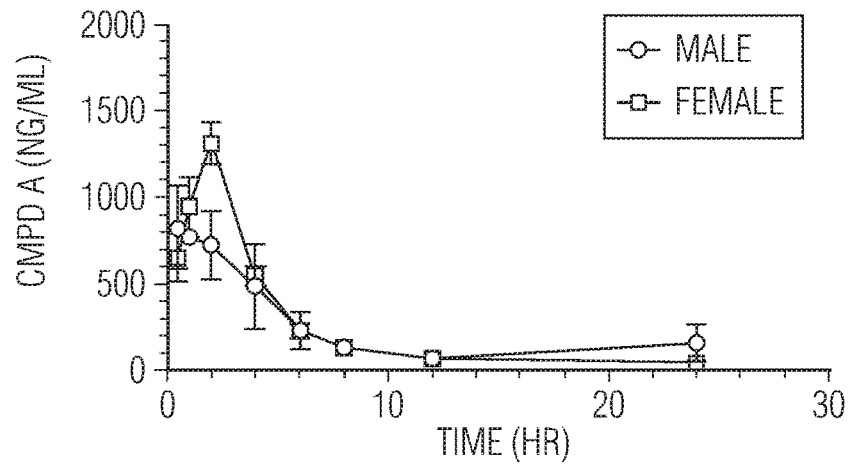

As shown in Table 6, the pharmacokinetics of all three formulations were comparable in both male and female dogs, but in male dogs the Tmax of the spray dried HPMC-AS formulation (Formulation 3) was four times faster than that of Formulations 1 and 2. The kinetics of each formulation as measured in dog plasma are shown in FIGS. 12A-C.

Figure 13:
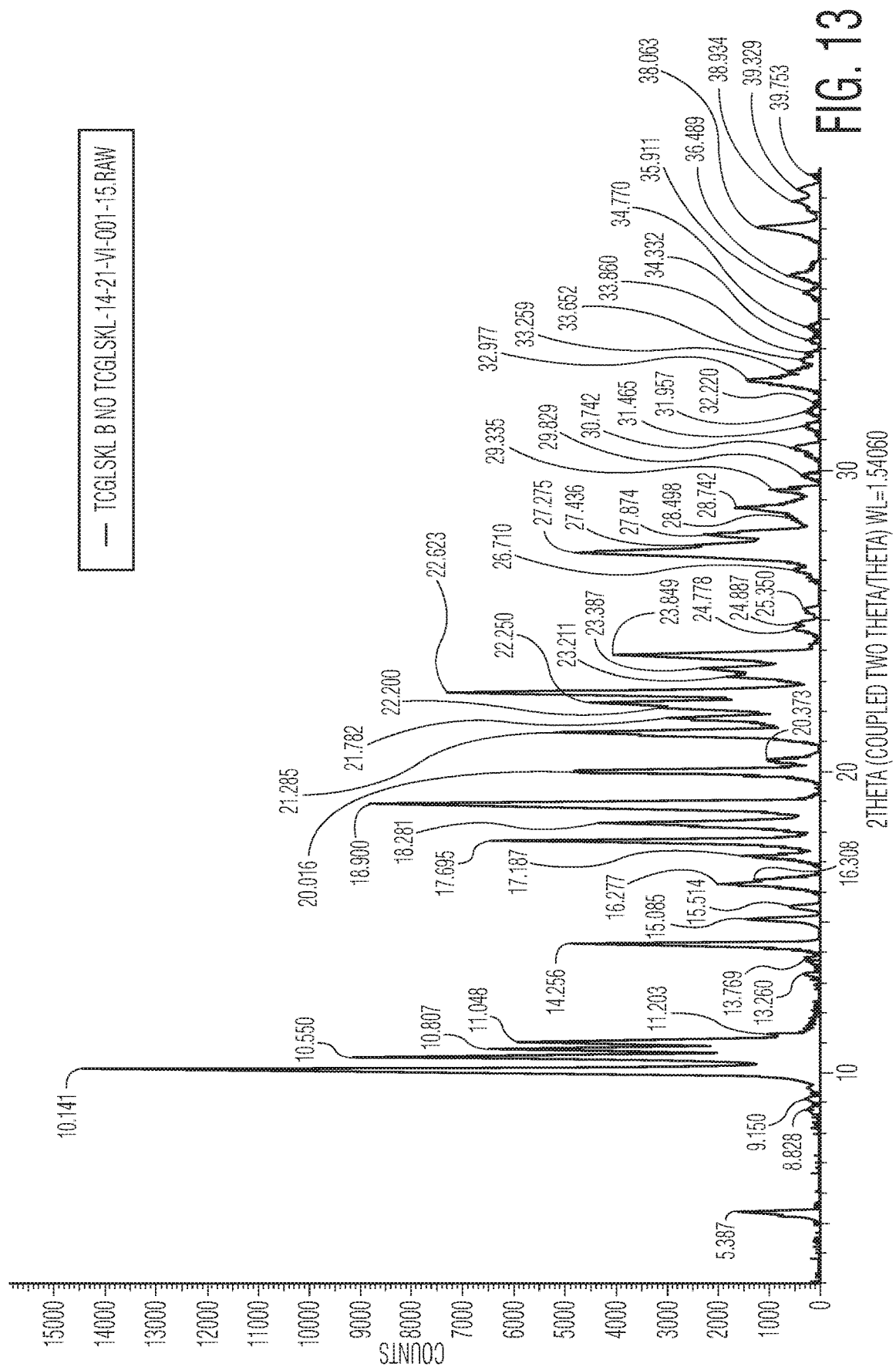
FIG. 13 is an XRPD spectrum of a stable crystalline polymorph of N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide which is used to manufacture formulations of the disclosure.

Example 7—Stable Crystalline Polymorph of N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide A stable crystalline polymorph of the active ingredient N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide was made by dissolving the solid active ingredient in acetone under heat, allowing the resulting solution to cool to 40-50° C., filtering the cooled solution to remove any insoluble particulate matter to produce a filtrate, and evaporating the filtrate under reduced pressure to obtain a crystalline solid. The crystalline solid was then dried under vacuum at 60-65° C. The stable crystalline polymorph thus obtained is characterized by the XRPD spectrum shown in FIG. 13.

The stable crystal polymorph was used to manufacture formulations of the disclosure as described in the Examples above.

Example 8—PK Characteristics in Humans

A pharmaceutical formulation of the disclosure comprising the active ingredient N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide was evaluated for safety/tolerability and preliminary efficacy in eligible human subjects with advanced solid tumors, and the pharmacokinetic (PK) profile of the active ingredient was investigated for each subject. Eligibility criteria for inclusion in this study included:
Male or female at least 18 years of age
Histological diagnosis of metastatic cancer per study design criteria
ECOG Performance Status 0-1
Adequate end organ function
≤Grade 1 hemoglobin, platelets, and ANC
≤Grade 1 creatinine, ALT/AST
Total bilirubin≤2×ULN
HbA1c≤ULN or fasting glucose<140 mg/dL.

Fifteen eligible patients were enrolled in total daily dose levels ranging from 10-800 mg per day of the active ingredient, provided as 10-mg, 20-mg, 80-mg and 120-mg tablets for oral administration. Dose escalation is ongoing. All study medication supplies were provided by Asana BioSciences, LLC (Bridgewater, N.J.). The tablets were administered orally every 12-24 hours on an empty stomach (either 1 hour before or 2 hours after a meal or snack) with approximately 240 mL of water. On study days in which there was a single plasma PK sample taken, the subject was instructed to fast for at least 2 hours prior to collection of the PK sample. On study days with multiple plasma PK samples taken, the subject was instructed to fast overnight (at least 8 hours prior to study drug administration) and remain fasting for 2 hours after study drug administration. The date and time of the dose(s) taken prior to or on PK sampling days were collected by the study site or catalogued via a diary card provided to the subject.

Figure 14A:
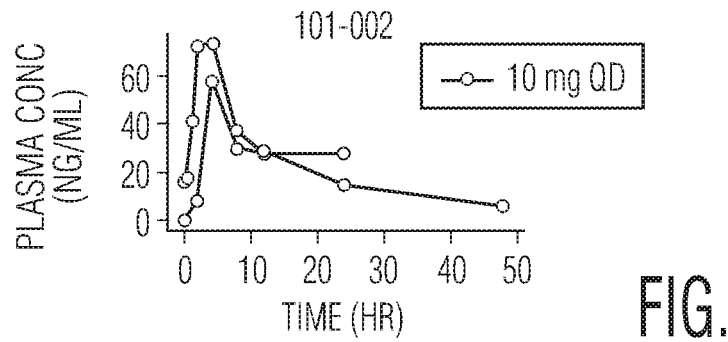
FIGS. 14A to 14N are graphs showing individual Plasma Concentrations of CMPD A in nanograms per milliliter (ng/mL) over nominal time in in hours (h) for different human subjects at different doses of CMPD A, at different time points post-treatment.
Figure 14B:
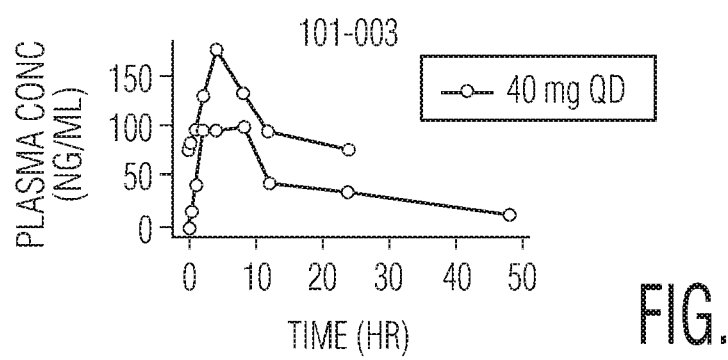
FIG. 14B: Patient 101-003 at a 240 mg QD.
Figure 14C:
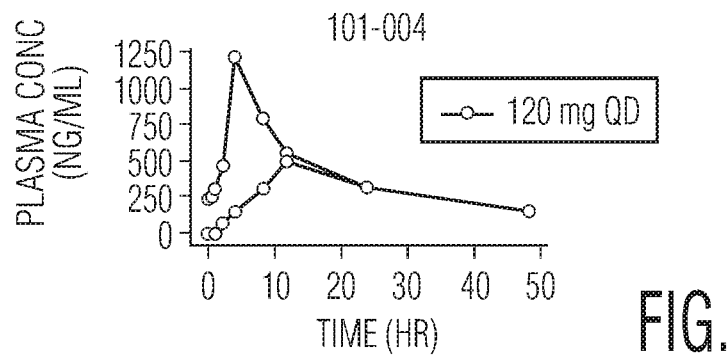
FIG. 14C: Patient 101-004 at 120 mg QD.
Figure 14D:
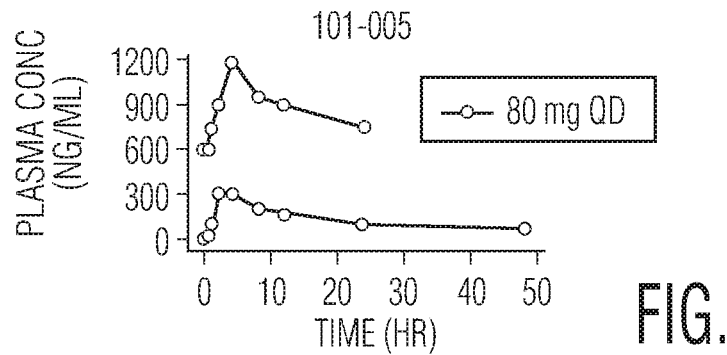
FIG. 14D: Patient 101-005 at 80 mg QD.
Figure 14E:
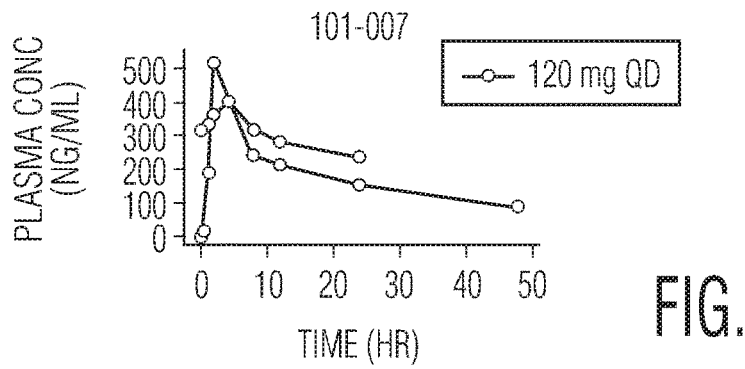
FIG. 14E: Patient 101-007 at 120 mg QD.
Figure 14F:
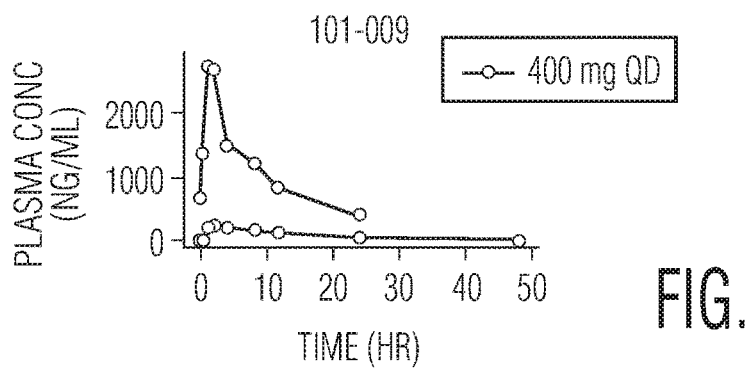
FIG. 14F: Patient 101-009 at a 400 mg QD.
Figure 14G:
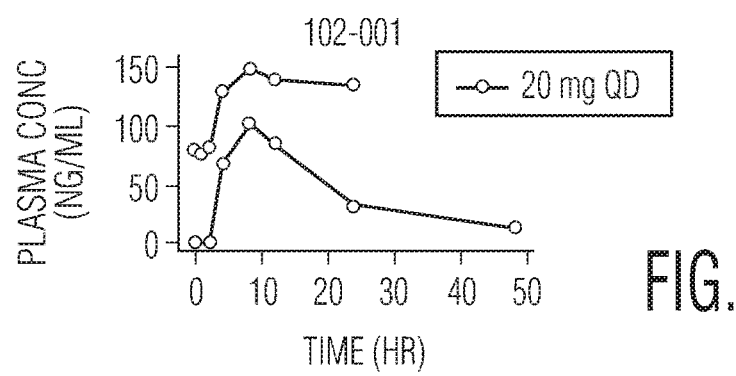
FIG. 14G: Patient 102-001 at 20 mg QD.
Figure 14H:
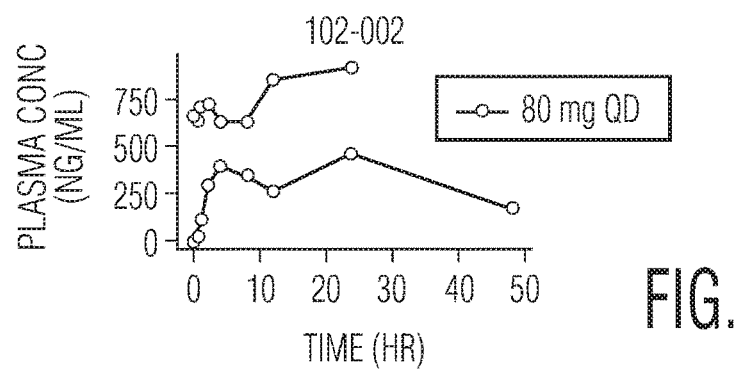
FIG. 14H: Patient 102-002 at 80 mg QD.
Figure 14I:
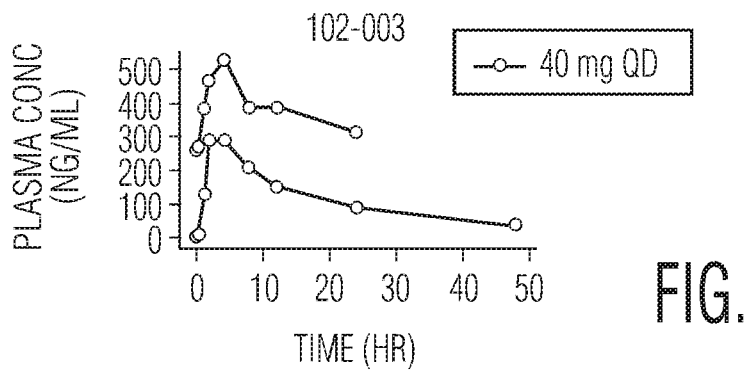
FIG. 14I. Patient 102-003 at 40 mg QD.
Figure 14J:
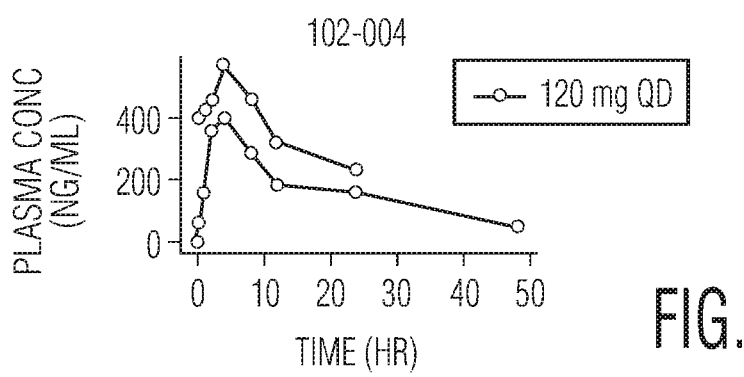
FIG. 14J: Patient 102-004 at 120 mg QD.
Figure 14K:
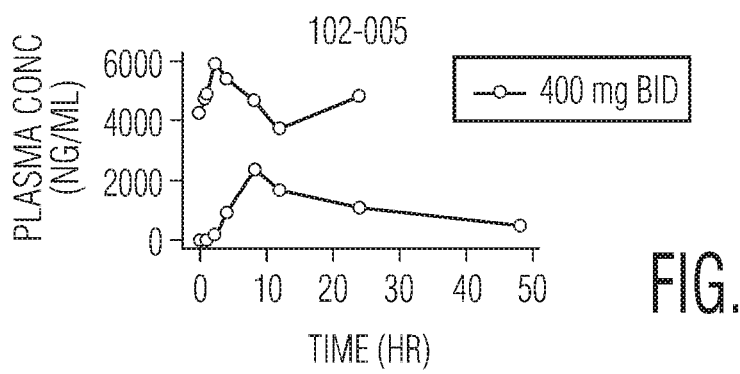
FIG. 14K: Patient 102-005 at 400 mg BID.
Figure 14L:
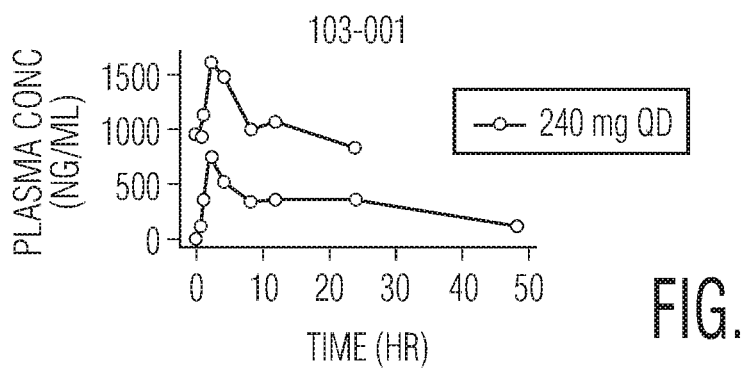
FIG. 14L: Patient 103-001 at 240 mg QD.
Figure 14M:
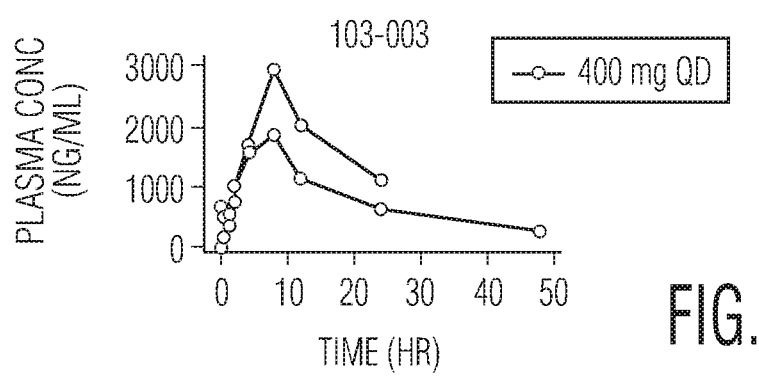
FIG. 14M: Patient 103-003 at 400 mg QD.
Figure 14N:
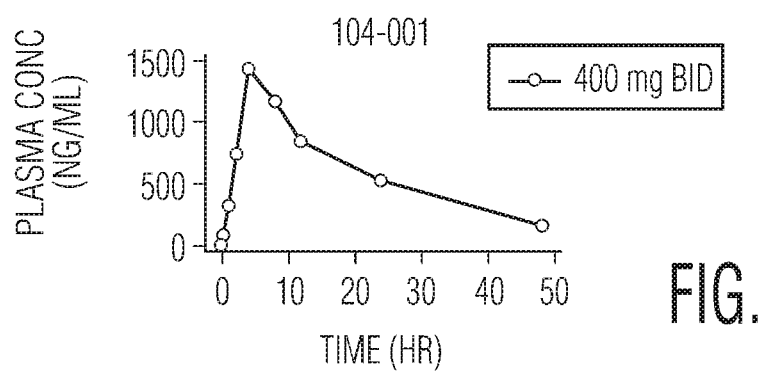

An ultra performance liquid chromatographic method was used for the determination of the active ingredient in human EDTA K2 plasma. This method was validated over an analytical range of 0.5 to 500 ng/mL. Calibration standards (CS) and quality control (QC) samples at three or four levels of concentrations were prepared fresh from the appropriate working solutions which were stored at −20° C. The human EDTA K2 plasma used for the preparation of CS and QC samples was obtained from Bioreclamation (Westbury, Pa., USA) and analyzed to determine possible interference with the analyte or the internal standard, and no significant interference was observed. The following parameters were used to determine analyte levels in the plasma samples:
Biological Matrix: Human EDTA K2 plasma
Assay Volume Required: 0.050 mL
Sample Extraction: Automated protein precipitation
Type of Assay: LC/MS/MS (API 4000)
Column: ACE Excel 2 C18, 50×3.0 mm, 2 μm
Mobile Phase A: Milli-Q type water with ammonium formate
Mobile Phase B: Acetonitrile
Chromatographic Integration/Acquisition Data System: Analyst 1.6.1, AB Sciex
LIMS: Watson version 7.4.1, Thermo Fisher Scientific Corporation
Quantitation Method: Peak area ratio
Calibration Regression: Linear
Weighting Factor: 1/C2
Calibration Equation: y=mx+b
Determination Factor: r2
Analyte Retention Time: 1.15 minutes
IS Retention Time: 1.12 minutes
Acquisition Time: 3.50 minutes
Preliminary plasma concentrations in ng/mL over nominal time in hours for given subjects at given active ingredient (CMPD A) dosage levels are shown in FIGS. 14A-N. The dosage levels for FIGS. 14A-N are 10 mg QD, 20 mg QD, 40 mg QD, 80 mg QD, 120 mg QD, 240 mg QD, 400 mg QD, and 400 mg BID.

Figure 15:
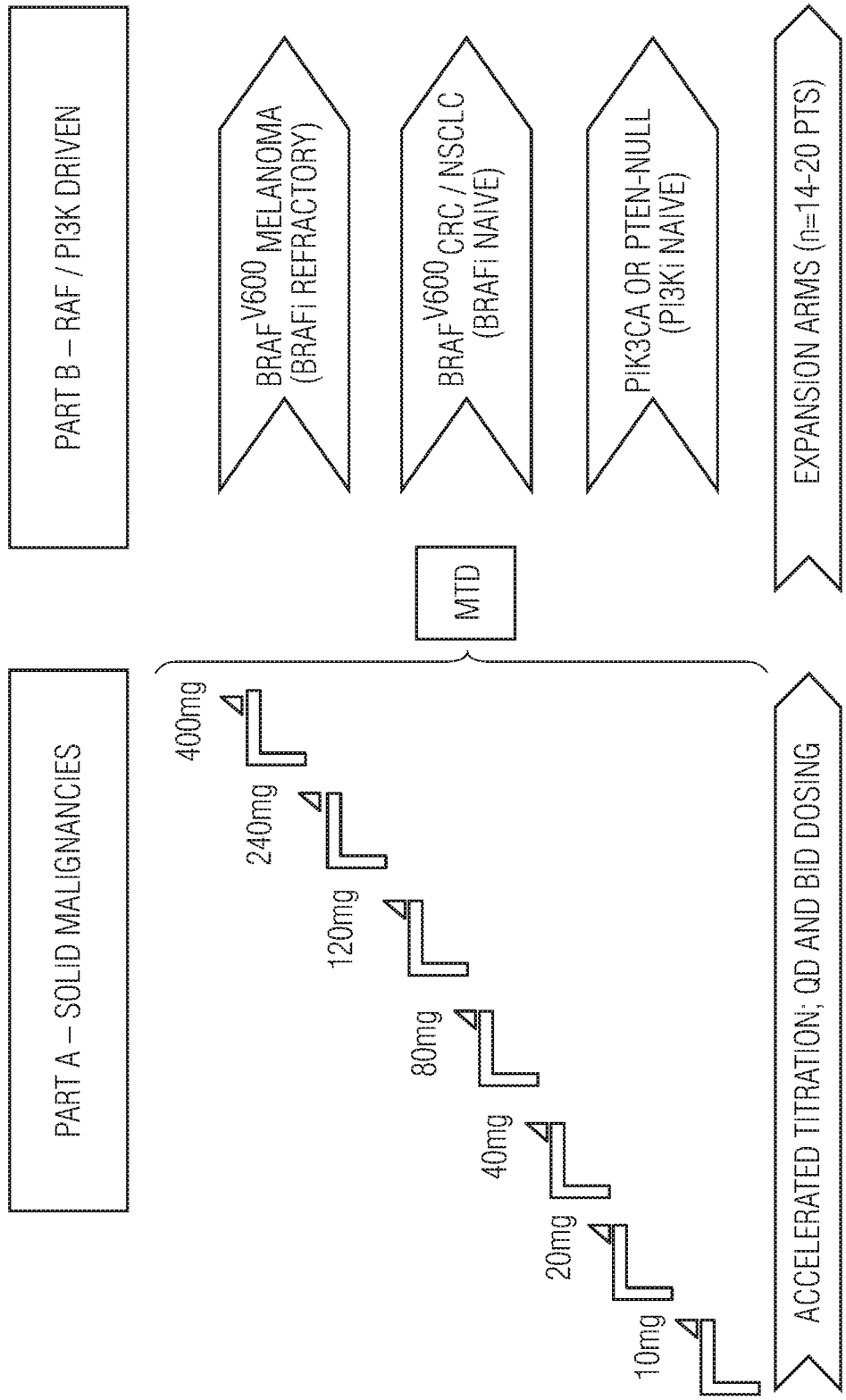
FIG. 15 shows the clinical trial design used in Examples 8 and 9 of the present disclosure.

The pharmaceutical formulation of the disclosure discussed in Example 8 above was evaluated for safety/tolerability and preliminary efficacy in eligible human subjects with advanced solid tumors. The clinical trial design followed in Example 8 of this disclosure is shown in FIG. 15, and the patient demographics and disposition of the subjects tested in Example 8 are given in Table 7 below.

TABLE 7

| Cohort (Dose) | Subject (Age/Race/Gender) | Diagnosis/Status Summary |
| --- | --- | --- |
| Cohort 8 (400 mg BID) | 102-005 (52/W/M) | Melanoma (BRAFv600e)/Ongoing-Cycle 1 |
| Cohort 7 (400 mg QD) | 101-009 (46/W/M) | Rectal (KRAS)/Discontinued RECIST PD |

TABLE 7-continued

| Cohort (Dose) | Subject (Age/Race/Gender) | Diagnosis/Status Summary |
|---|---|---|
| additional 240 mg QD | 101-008 (59/W/M) | Colon (KRAS)/Discontinued RECIST PD |
| Cohort 6 (240 mg QD) | 103-001 (59/W/F) | Cholangiocarcinoma (PIK3CA)/Ongoing-Cycle 3 |
| additional 120 mg QD | 102-004 (62/W/F) | Pancreatic (KRAS)/Discontinued, RECIST PD |
| additional 120 mg QD | 101-007 (59/W/M) | Colon (NRAS)/Discontinued, RECIST PD |
| Cohort 5 (120 mg QD) | 101-004 (74/W/F) | Melanoma (BRAFv600e)/Discontinued, RECIST PD |
| additional 80 mg QD | 101-005 (48/W/M) | Colon (PI3Kca, KRAS)/Discontinued, RECIST PD |
| Cohort 4 (80 mg QD) | 102-002 (631W/F) | Appendix adenocarcinoma (BRAF, KRAS)/ Discontinued, RECIST PD |
| additional 40 mg QD | 102-003 (691W/F) | Parotid myoepithelial carcinoma (PI3Kca)/ Discontinued, RECIST PD |
| Cohort 3 (40 mg QD) | 101-003 (691W/F) | Endometrial adenocarcinoma (PIK3ca, KRAS)/ Discontinued, RECIST PD |
| Cohort 2 (20 mg QD) | 102-001 (33/W/M) | Duodenal adenocarcinoma (AKT1, EFGR, c-MET)/ Discontinued, SAE, RECIST PD |
| Cohort 1 (10 mg QD) | 101-002 (66/W/M) | NSCLC (KRAS)/Discontinued, RECIST PD |

Pharmacokinetic parameters were determined as described in Example 8 above and showed moderate inter-subject variability and a generally dose-dependent Cmax and AUC (see also FIGS. 16A and 16B), and that moderate rates of oral absorption and elimination (t½: 10-25 hours). An approximately 2-fold accumulation in AUC at steady state was observed; Effective t½~24 hrs. Via the clinical trial outlined in Example 8 of this disclosure, oral doses of a pharmaceutical formulation of the disclosure was evaluated for safety/tolerability and preliminary efficacy in eligible patients with advanced solid tumors, using an accelerated dose titration design and enrolling cohorts of melanoma, CRC and NSCLC patients with a BRAF, PIK3CA or PTEN mutation at MTD. Patient accrual is ongoing. To date, fifteen eligible patients have been enrolled in dose levels ranging from 10-400 mg QD and 400 mg BID. The active ingredient has been well tolerated. Treatment-related adverse events (TRAEs) were mild (G1) to moderate (G2). TRAEs include diarrhea (G2) (n=1), hyperglycemia (G2) (N=1), rash macula-papular (G2) (n=1), vomiting (G1) (n=3), nausea (G1) (n=2), hyperglycemia (G1) (n=2) and dry mouth/lips/skin, transient blurred vision, rash acneiform, ALT increased, cognitive disturbance and hyperkalemia (G1) (n=1). Transient G2 and G1 elevation of glucose and insulin c-peptide levels has been noted in 3 pts. No G3/4 AEs have been observed to date. Dose escalation is ongoing. Overall, these data indicate that the active ingredients comprising pharmaceutical formulations of the disclosure, in particular N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide, are first-in-class dual B-RAF and PI3K inhibitors useful for the potential treatment of subjects with B-RAF and/or PI3K-driven cancers.

Tables 9 and 10 below shows the preliminary human steady-state pharmacokinetic parameters of CMPD A in cancer patients (individual or mean), which were determined as described in Example 8 above.

TABLE 9

| Dose (mg) | n | Cmax (ng/mL) | Tmax (hr) | $AUC_{0-24h}$ (ng · hr/mL) | Cmin (ng/mL) |
|---|---|---|---|---|---|
| 10 QD | 1 | 74 | 4 | 912 | 16.0 |
| 20 QD | 1 | 149 | 8 | 3160 | 76.4 |
| 40 QD | 2 | 348 | 4 | 5890 | 167 |
| 80 QD | 2 | 1055 | 14 | 20100 | 614 |
| 120 QD | 3 | 728 | 4 | 10100 | 239 |
| 240 QD | 2 | 954 | 2 | 14900 | 463 |
| 400 QD | 2 | 2850 | 4.5 | 33400 | 589 |
| 400 BID | 1 | 5990 | 2 | 110000 | 3718 |

Dose-dependent Cmax and AUC
Approximately 2-fold accumulation for QD and ~3-fold accumulation for BID administration
Moderate rate of elimination ($t_{1/2}$ 10-25 hours)
Moderate to high inter-and intra-subject variability

TABLE 10

| | | | | | | | | |
|---|---|---|---|---|---|---|---|---|
| | | | Human PK Parameters (individual and mean) for CMPD A | | | | | |
| Day | Dose (mg) | n | Cmax (ng/mL) | Tmax (hr) | $AUC_{0-24}$ (ng · hr/mL) | $T_{1/2}$ (hr) | $R_{Cmax}$ | $R_{AUCtau}$ |
| 1 | 10 | 1 | 58.0 | 4 | 622 | 16.1 | | |
| | 20 | 1 | 101 | 8 | 1480 | 13.7 | | |
| | 40* | 2 | 192 | 5 | 2670 | 17.9 | | |
| | | | (96.2, 289) | (8, 2) | (1400, 5510) | (18.2, 17.6) | | |
| | 80* | 2 | 384 | 14 | 6050 | NC | | |
| | | | (470, 300) | (24, 4) | (8090, 4010) | (NC, 22.4) | | |
| | 120** | 3 | 509 | 4 | 6660 | 24.9 | | |
| | | | (±13) | (2, 12) | (±1250) | (±4.8) | | |
| | 240* | 2 | 520 | 5 | 6930 | 17.5 | | |
| | | | (744, 295) | (2, 8) | (9560, 4300) | (23.9, 11.0) | | |

TABLE 10-continued

| | Human PK Parameters (individual and mean) for CMPD A | | | | | | | |
|---|---|---|---|---|---|---|---|---|
| Day | Dose (mg) | n | Cmax (ng/mL) | Tmax (hr) | $AUC_{0-24}$ (ng · hr/mL) | $T_{1/2}$ (hr) | $R_{Cmax}$ | $R_{AUCtau}$ |
| | 400 QD | 2 | 1067 (264, 1870) | 2 | 15000 (3200, 26700) | 15.4 (15.2, 15.6) | | |
| | 400 bid | | 1880 (2330, 1430) | 6 (8, 4) | 26300 (32100, 20400) | 18.6 (22.5, 15.0) | | |
| 15 | 10 | 1 | 74 | 4 | 912 | NC | 1.3 | 1.5 |
| | 20 | 1 | 149 | 8 | 3160 | 127 | 1.5 | 2.1 |
| | 40* | 2 | 348 (173, 523) | 4 (4, 4) | 5890 (2580, 9190) | 35.1 (22.5, 47.8) | 1.8, 1.8 | 1.9, 2.3 |
| | 80* | 2 | 1055 (931, 1179) | 14 (24, 4) | 20100 (19000, 21300) | NC (NC, 48.7) | 2.0, 4.0 | 2.4, 5.3 |
| | 120** | 3 | 728 (±434) | 4 (4, 4) | 10100 (±3680) | 24.1 (±15.8) | 0.8-2.4 | 1.2-1.9 |
| | 240* | 2 | 954 (1610, 299) | 2 (2, 2) | 14900 (26000,3740) | 19.7 (29.0, 10.3) | 2.2, 1.0 | 2.7, 0.9 |
| | 400 QD | 2 | 2850 (2770, 2930) | 4.5 (1, 8) | 33400 (25500, 41300) | 10.9 (10.1, 11.7) | 10.5, 1.57 | 8.0, 1.55 |
| | 400 bid | 1 | 5900 | 2 | 110000 | — | 2.53 | 3.76 |

Example 10—Mouse Xenograft Models

A. ST052C Tumor Model

Figure 17A:
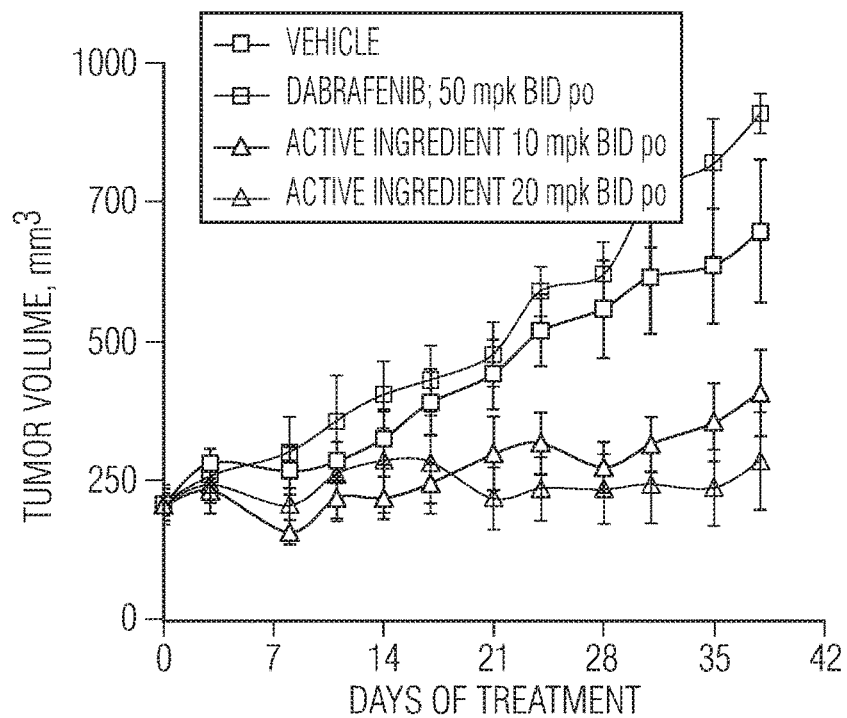
FIGS. 17A and 17B are graphs showing inhibition of tumor growth in a mouse xenograft model of vemurafinib-resistant cancer (FIG. 17A) and a mouse xenograft model of vemurafinib-sensitive melanoma (FIG. 17B), each treated with a vehicle control, and two doses of an active ingredient of the present disclosure.

The ST052C tumor is derived from a patient who had acquired resistance to Vemurafenib. The tumor harbors the B-RAFV600E mutation and an acquired PIK3CA mutation. ST052C tumor cells were implanted into mice to form xenograft tumors, and the mice were dosed orally BID in four treatment groups: 1) vehicle control; 2) Dabrafenib; 50 mpk; 3) active ingredient (N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide) at 10 mg/kg; and 4) the same active ingredient at 20 mg/kg. FIG. 17A shows a dose-dependent inhibition of tumor growth for the active ingredient over the vehicle control and dabrafenib.

B. ST052B Tumor Model

Figure 17B:
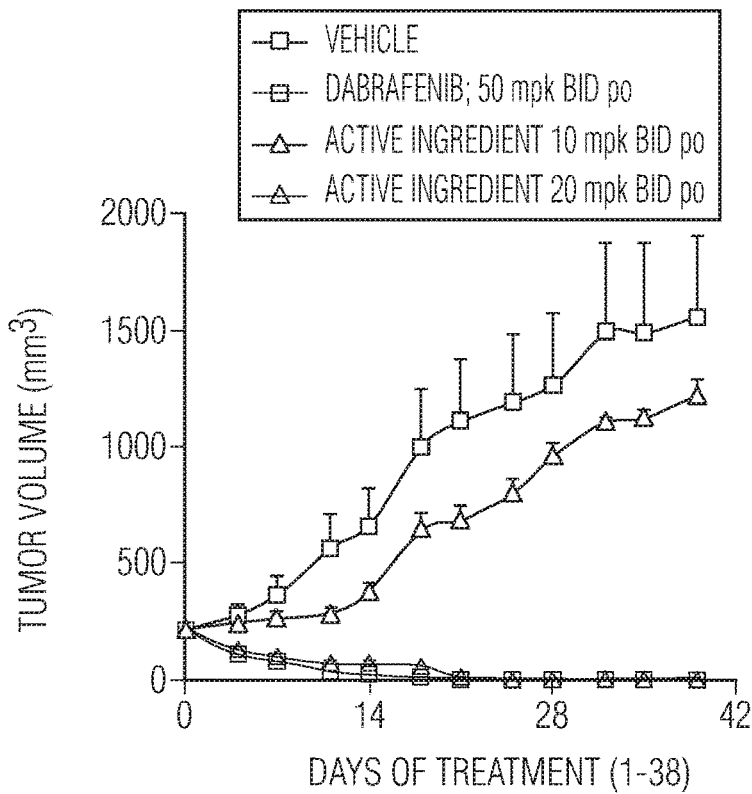

The ST052B tumor is derived from a melanoma patient prior to treatment with vemurafenib. ST052B tumor cells were implanted into mice to form xenograft tumors, and the mice were dosed orally BID in four treatment groups: 1) vehicle control; 2) Dabrafenib; mpk; 3) active ingredient (N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide) at 10 mg/kg; and 4) the same active ingredient at 20 mg/kg. FIG. 17B shows a dose-dependent inhibition of tumor growth for the active ingredient at 20 mg/kg and dabrafenib over the vehicle control.

Combination with Anti-PD1 Antibody

Figure 18:
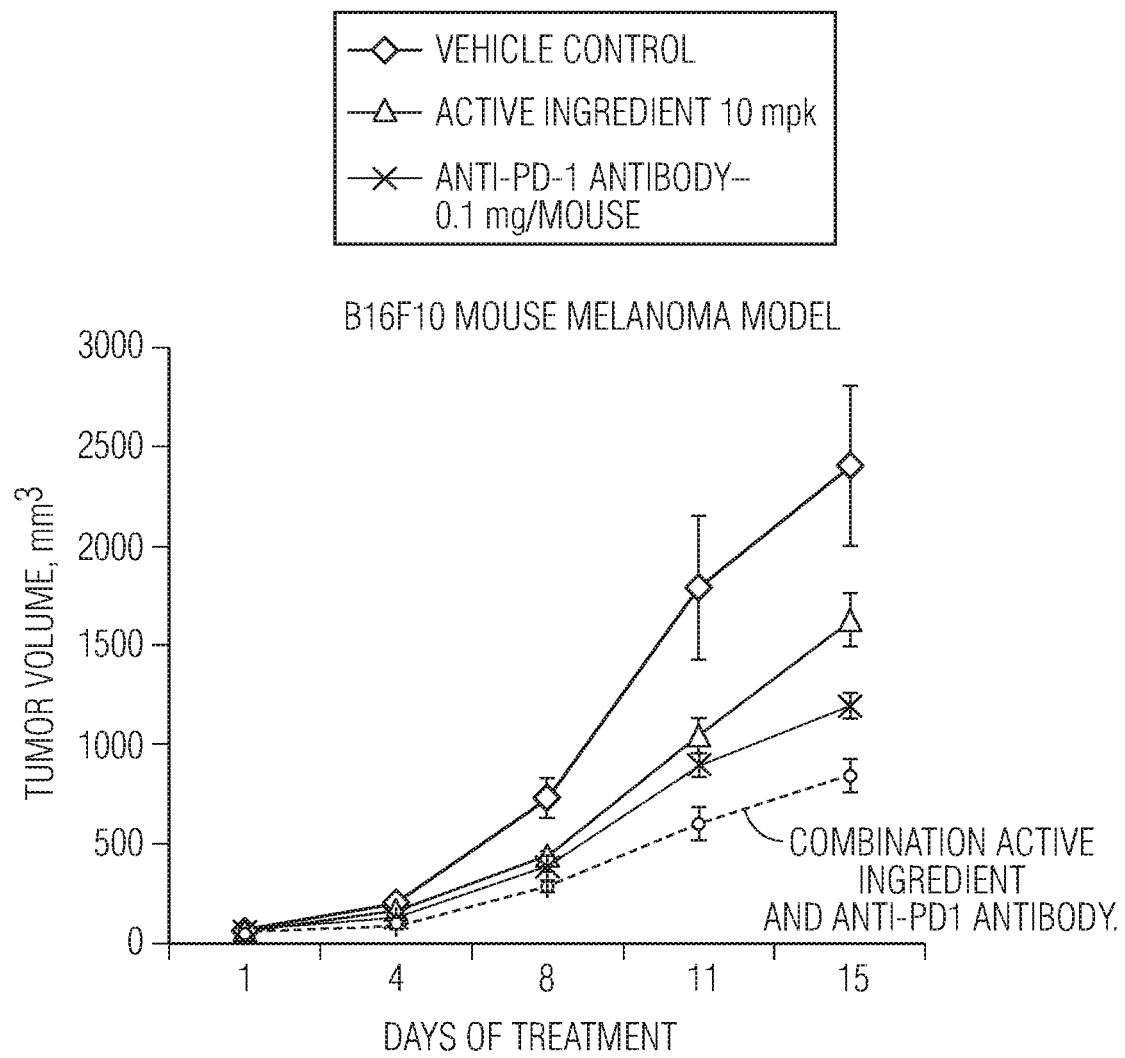
FIG. 18 is a graph showing inhibition of tumor growth in a mouse melanoma model in mice treated with a vehicle control, an active ingredient of the present disclosure, an anti-PD1 antibody, and a combination of an active ingredient of the present disclosure and an anti-PD1 antibody.

The active ingredient N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide was given orally in a B16F10 mouse melanoma model in four test groups as follows: 1) vehicle control; 10 mg/kg active ingredient; 2) 0.1 mg/mouse anti-PD1 antibody; 4) combination of 10 mg/kg active ingredient and 0.1 mg/mouse anti-PD1 antibody. As shown in FIG. 18, the combination of active ingredient and anti-PD1 antibody showed an additive effect with respect to inhibition of tumor growth.

While the present disclosure has been discussed in terms of certain embodiments, it should be appreciated that the present disclosure is not so limited. The embodiments are explained herein by way of example, and there are numerous modifications, variations and other embodiments that can be employed that would still be within the scope of the present disclosure.

The invention claimed is:

1. A pharmaceutical formulation comprising an active ingredient in substantially amorphous form and one or more stabilizing polymers, wherein the active ingredient comprises a compound of the formula:

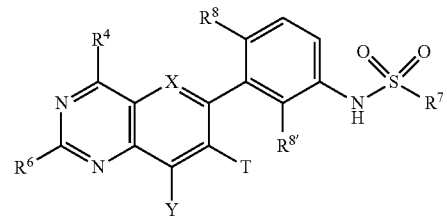

Wherein X is N, Y is H or optionally substituted $C_1$-$C_6$ alkyl; $R^4$ is morpholine optionally substituted with by $C_1$-$C_6$ alkyl; $R^7$ is $C_1$-$C_6$ alkyl optionally substituted by one or more F; $R^{8'}$ is halogen; and $R^6$ is

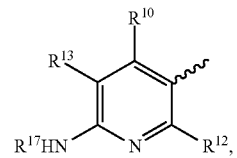

wherein $R^{10}$ is H, $C_1$-$C_6$ alkyl, halogen, CN or $CF_3$; $R^{12}$ is H or halogen; $R^{13}$ is H, halogen or $C_1$-$C_6$ alkyl; and $R^{17}$ is H, $C_1$-$C_6$ alkyl, ($C_1$-$C_6$ alkyl)-$NH_2$; and enantiomers, pharmaceutically acceptable salts and free bases thereof, wherein the active ingredient remains in substantially amorphous form after storage of the pharmaceutical formulation for a predetermined time and conditions.

2. The formulation of claim 1, wherein the predetermined time and conditions are at least about 4 weeks at 40° C./75% RH in a closed container.

3. The formulation of claim 1, wherein the predetermined time and conditions are at least about 1 week 25° C./60% RH in an open container.

4. The formulation of claim 1, wherein the formulation is spray dried.

5. The formulation of claim 4, wherein the active ingredient is deposited onto a particulate carrier.

6. The formulation of claim 5, wherein the active ingredient is deposited onto a particulate carrier by spray granulation or bead layering.

7. The formulation of claim 5, wherein the particulate carrier comprises mannitol.

8. The formulation of claim 1, wherein the one or more stabilizing polymers comprises a polyvinylpyrrolidone polymer.

9. The formulation of claim 1, wherein the one or more stabilizing polymers comprises hydroxypropylmethyl cellulose acetate succinate.

10. The formulation of claim 9, wherein the hydroxypropylmethyl cellulose acetate succinate has:
% methoxy of about 22.3 to 22.6, a % hydroxypropoxy of about 6.7 to 7.0, a % succinoyl of about 18.1 to 14 and a % acetyl of about 5.7 to 8.4 and dissolves in a pH of greater than or equal to about 5.5;
% methoxy of about 22.7 to 23.1, a % hydroxypropoxy of about 6.9 to 7.1, a % succinoyl of about 14.2 to 9.9 and a % acetyl of 7.5 to 10.6 and dissolves in a pH of greater than or equal to about 6.0; or
% methoxy of about 23.5 to 23.8, a % hydroxypropoxy of about 7.2 to 7.4, a % succinoyl of about 8.0 to 4.1 and a % acetyl of about 10.7 to 13.9 and dissolves in a pH of greater than or equal to about 6.5.

11. The formulation of claim 1, wherein the active ingredient is a free base.

12. The formulation of claim 1, wherein the active ingredient is selected from the group consisting of:
N-(3-(2-(2-aminopyrimidin-5-yl)-4-morpholinopyrido[3,2-d]pyrimidin-6-yl)-2-fluorophenyl)-3-fluoropropane-1-sulfonamide;
N-(3-(2-(6-aminopyridin-3-yl)-4-morpholinopyrido[3,2-d]pyrimidin-6-yl)-2-fluorophenyl)-3-fluoropropane-1-sulfonamide;
3-fluoro-N-(2-fluoro-3-(4-morpholino-2-(1H-pyrrolo[2,3-b]pyridin-5-yl)pyrido[3,2-d]pyrimidin-6-yl)phenyl)propane-1-sulfonamide;
N-(3-(2-(6-amino-4-(trifluoromethyl)pyridin-3-yl)-4-morpholinopyrido[3,2-d]pyrimidin-6-yl)-2-fluorophenyl)-3-fluoropropane-1-sulfonamide;
3-fluoro-N-(2-fluoro-3-(2-(6-(methylamino)pyridin-3-yl)-4-morpholinopyrido[3,2-d]pyrimidin-6-yl)phenyl)propane-1-sulfonamide;
(S)—N-(3-(2-(6-amino-4-fluoropyridin-3-yl)-4-(3-methylmorpholino)pyrido[3,2-d]pyrimidin-6-yl)-2-fluorophenyl)-3-fluoropropane-1-sulfonamide; and
(S)—N-(3-(2-(6-amino-4-(trifluoromethyl)pyridin-3-yl)-4-(3-methylmorpholino)pyrido[3,2-d]pyrimidin-6-yl)-2-fluorophenyl)-3-fluoropropane-1-sulfonamide.

13. The formulation of claim 1, comprising a ratio of the active ingredient to the one or more stabilizing polymers of about 1:4.

14. The formulation of claim 1, wherein the formulation comprises less than about 5000 ppm acetone.

15. The formulation of claim 1, wherein the formulation further comprises one or more anti-static agents.

16. The formulation of claim 15, wherein the one or more anti-static agents comprise colloidal silicon dioxide.

17. The formulation of claim 16, further comprising additional excipients comprising one or more binders, one or more tableting fillers, one or more disintegrants, and one or more surfactants.

18. The formulation of claim 17, wherein the one or more binders comprise mannitol, the one or more tableting fillers comprise microcrystalline cellulose, the one or more disintegrants comprise crospovidone, and the one or more lubricants comprise magnesium stearate.

19. The formulation of claim 17, wherein the one or more stabilizing polymers, active ingredient, one or more anti-static agents and additional excipients are compressed into one or more tablets.

20. The formulation of claim 19, wherein the one or more tablets are coated.

21. The formulation of claim 19, wherein the amount of active ingredient per tablet is about 10 to 100 mg.

22. The formulation of claim 1, wherein the formulation is loaded into one or more capsules.

23. The formulation of claim 22, wherein the amount of active ingredient per capsule is about 25 to 75 mg.

24. The formulation of claim 1, wherein the formulation is combined with an aqueous or semi-solid carrier.

25. The formulation of claim 24, wherein the formulation combined with an aqueous carrier comprises a liquid dispersion.

26. The formulation of claim 25, wherein the aqueous carrier comprises about 2% w/V hydroxypropyl cellulose and about 0.1% w/V polysorbate 80 in water.

27. The formulation of claim 24, wherein the semi-solid carrier comprises a food item.

28. A kit comprising one or more dosage forms and instructions for administering the dosage forms to a subject, wherein the dosage forms comprise a pharmaceutical formulation comprising an active ingredient in substantially amorphous form and one or more stabilizing polymers, wherein the active ingredient comprises a compound of the formula:

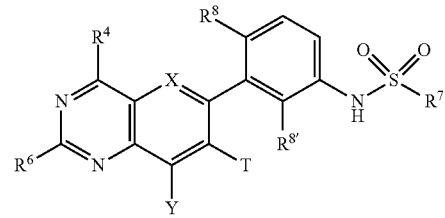

wherein X is N, Y is H or optionally substituted $C_1$-$C_6$ alkyl; $R^4$ is morpholine optionally substituted with by $C_1$-$C_6$ alkyl; $R^7$ is $C_1$-$C_6$ alkyl optionally substituted by one or more F; $R^{8'}$ is halogen; and $R^6$ is

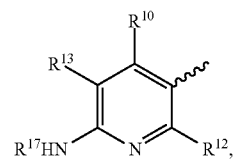

wherein $R^{10}$ is H, $C_1$-$C_6$ alkyl, halogen, CN or $CF_3$; $R^{12}$ is H or halogen; $R^{13}$ is H, halogen or $C_1$-$C_6$ alkyl; and $R^{17}$ is H, $C_1$-$C_6$ alkyl, ($C_1$-$C_6$ alkyl)-$NH_2$; and, pharmaceutically acceptable salts and free bases thereof, wherein the active ingredient remains in substantially amorphous form after storage of the pharmaceutical formulation for a predetermined time and conditions.

* * * * *